(12) United States Patent
Munson et al.

(10) Patent No.: US 7,141,429 B2
(45) Date of Patent: Nov. 28, 2006

(54) USE OF LIQUID JUNCTION POTENTIALS FOR ELECTROPHORESIS WITHOUT APPLIED VOLTAGE IN A MICROFLUIDIC CHANNEL

(75) Inventors: Matthew S. Munson, Gaithersburg, MD (US); Catherine R. Cabrera, Cambridge, MA (US); Paul Yager, Seattle, WA (US); Anson Hatch, Seattle, WA (US); Andrew Kamholz, Seattle, WA (US)

(73) Assignee: University of Washington, Seattle, WA (US)

( * ) Notice: Subject to any disclaimer, the term of this patent is extended or adjusted under 35 U.S.C. 154(b) by 558 days.

(21) Appl. No.: 10/268,620

(22) Filed: Oct. 9, 2002

(65) Prior Publication Data

US 2003/0102214 A1    Jun. 5, 2003

Related U.S. Application Data

(60) Provisional application No. 60/328,328, filed on Oct. 9, 2001.

(51) Int. Cl.
*G01N 35/08* (2006.01)
*B01D 17/00* (2006.01)

(52) U.S. Cl. ............................ 436/53; 436/52; 210/511
(58) Field of Classification Search ............ 204/450, 204/451, 454, 459, 468, 600, 601, 627; 422/101; 210/511, 634; 436/52, 53
See application file for complete search history.

(56) References Cited

U.S. PATENT DOCUMENTS 6,454,945 B1 * 9/2002 Weigl et al. ................ 210/634

6,685,809 B1 * 2/2004 Jacobson et al. ........... 204/450

OTHER PUBLICATIONS

Bard and Faulkner, Eds., *Electrochemical Methods: Fundamentals and Applications*, 2nd ed., John Wiley and Sons, New York, 2001, p. 64.
Beard, D. A., "Response to 'Comment on Taylor dispersion of a solute in a microfluidic channel'" (Dec. 2001) *J. Appl. Phys.*, 90(12):6555-6556.
Beard, D. A., "Taylor dispersion of a solute in a microfluidic channel," (Apr. 2001) *J. Appl. Phys.*, 89(8):4667-4669.
Becker, H. and C. Gärtner, "Polymer microfabrication methods for microfluidic analytical applications," (Jan. 2000) *Electrophoresis* 21(1):12-26.
Becker, H. and L.E. Locascio, "Polymer microfluidic devices," (Feb. 2002) *Talanta*, 56(2):267-287.
Beebe, D.J. et al., "Physics and applications of microfluidics in biology," (Aug. 2002) *Annual Review of Biomedical Engineering*, 4:261-286.

(Continued)

*Primary Examiner*—Alex Noguerola
(74) *Attorney, Agent, or Firm*—Townsend and Townsend and Crew LLP

(57) ABSTRACT

This invention provides methods for using liquid junction potentials to control the transport of charged particles in fluid streams that are in laminar flow within microfluidic channels. Applications of the methods of this invention include sample preconditioning (removal of interfering substances), electrophoretic separation (fractionation) of charged particles, enhanced or delayed mixing of charged particles across a fluid interface relative to diffusion only, focusing charged particles in a fluid stream in one or two dimensions, and concentration of charged reactants at a fluid interface.

34 Claims, 19 Drawing Sheets

OTHER PUBLICATIONS

Bier, M. et al., "Electrophoresis: mathematical modeling and computer simulation," (1983) *Science* 219(4590):1281-1287.

Borchard, G., "Chitosans for gene delivery," (Nov. 2001) *Advanced Drug Delivery Reviews* 52:145-150.

Borge, G. et al., "On the liquid junction potential for the determination of equilibrium constants by means of the potentiometric technique without constant ionic strength," (1997) *J. Electroanal. Chem.*, 440:183-192.

Brody, J.P. et al., "Biotechnology at low Reynolds Nos.," (1996) *Biophys. J.*, 71:3430-3441.

Cabrera, C. R. et al., "Formation of natural pH gradients in a microfluidic device under flow conditions: model and experimental validation," (Feb. 2001) *Anal. Chem.* 73:658-666 [published on web Dec. 29, 2000].

Chan, C.K. and D.A. Jans, "Using nuclear targeting signals to enhance non-viral gene transfer," (Apr. 2002) *Immunology and Cell Biology* 80(2):119-130.

Chován, T. and A. Guttman, "Microfabricated devices in biotechnology and biochemical processing," (Mar. 2002) *Trends in Biotechnology* 20(3):116-122.

Christiansen, T. F., "The Achilles' heel of potentiometric measurements, the liquid junction potential," (1986) *IEEE Trans.Biomed. Eng.* 33:79-82.

Cobben, P.L. et al., "Chemically modified ion-sensitive field-effect transistors: elimination of the liquid junction potential in a double sensor flow-injection analysis cell," (1993) *Anal. Chim. Acta* 276:347-352.

Davis, M.E., "Non-viral gene delivery systems," (Apr. 2002) *Current Opinion in Biotechnology* 13(2):128-131.

De Jesus, O.L.P. et al., "Polyester dendritic systems for drug delivery applications: In vitro and in vivo evaluation" (2002) *Bioconjugate Chemistry* 13(3): 453-461 [published on Web Apr. 24, 2002].

Demas, J.N. et al., "Fluorescence detection in hydrohynamically focused sample streams: reduction of diffusional defocusing by association of analyte with high-molecular-weight species," (1998) *Appl. Spectrosc.* 52(5):755-762.

De Smedt, S.C. et al., "Cationic polymer based gene delivery systems," (Feb. 2000) *Pharmaceutical Research* 17(2):113-126.

Dorfman, K. D. and Brenner, H. "Comment on Taylor dispersion of a solute in a microfluidic channel," (Dec. 2001) *J. Appl. Phys.* 90(12):6553-6554

Førland, K.S. and Førland, T., "An alternative approach to electrochemistry," (1995) *J. Stat. Phys.* 78(1/2):513-529.

Godbey, W.T. et al.; "Poly(ethylenimine) and its role in gene delivery," (1999) *Journal of Controlled Release* 60:149-160.

Greenlee, R.D. and Ivory, C.F., "Protein focusing in a conductivity gradient," (1998) *Biotechnol. Prog.* 14:300-309.

Guggenheim, E.A., "A study of cells with liquid—liquid junctions," (1930) *J. Am. Chem. Soc.* 52:1315-1337.

Guggenheim, E.A., "The conceptions of electrical potential difference between two phases and the individual activities of ions," (1929) *J. Phys. Chem.* 33:842-849.

Harned, H. S., "Individual thermodynamic behaviors of ions in concentrated solutions including a discussion of the thermodynamic method of computing liquid junction potentials," (1926) *J. Phys. Chem.* 30:433-456.

Henderson, P., "Zur thermodynamik der flüssigkeitsketten," (1908) *Z. Phys. Chem.* 63:325-345 (in German).

Henderson, P., "Zur thermodynamik der flüssigkeitsketten," (1907) *Z. Phys. Chem.* 59:118-127 (in German).

Hennink, W.E. et al., "Pharmaceutical aspects of polymer-based non-viral gene delivery systems: experience with p(DMAEMA)-pCMV-lacZ polyplexes," (Jan.-Feb. 2001) *Stp. Pharma. Sciences* 11(1):11-19.

Henry, J. and Louro, B., "Asymptotic analysis of reaction-diffusion-electromigration systems," (1995) *Asymptotic Anal.* 10:279-302.

Jahn, H., "Über den dissociationsgrad und das dissociationgleichgewicht stark dissociierter elektrolyte," (1900) *Z. Phys. Chem.* 33:545-576 (in German).

Kamholz, A.E. et al., "Optical measurement of transverse molecular diffusion in a microchannel," (Apr. 2001) *Biophys. J.* 80:1967-1972.

Kamholz, A.E. and Yager, P., "Theoretical analysis of molecular diffusion in pressure-driven laminar flow in microfluidic channels," (Jan. 2001) *Biophys. J.* 80:155-160.

Kamholz, A.E. et al., "Quantitative analysis of molecular interactin in a microfluidic channel: the T-sensor," (1999) *Anal. Chem.* 71:5340-5347.

Lamb, A.B. and Larson, A.T., "Reproducible liquid junction potentials: the flowing junction," (1920) *J. Am. Chem. Soc.* 42:229-237.

Lewis, G.N., and Sargent, L.W., "Potentials between liquids," (1909) *J. Am. Chem. Soc.* 31:363-367.

Lichtenberg, J. et al., "Sample pretreatment on microfabricated devices," (Feb. 2002) *Talanta*, 56:233-266.

Lindgren, E.R. et al., "Numerical simulation of electrokinetic phenomena," in: Tedder, et al., Eds, Emerging Technologies in Hazardous Waste Management V,American Chemical Society: Washington, DC, 1995, pp. 48-62.

Lvov, S.N. and Macdonald, D.D., "Estimation of the thermal liquid junction potential of an external pressure balanced reference electrode," (1996) *J. Electroanal. Chem.* 403:25-30.

MacInnes, D.A. and Yeh, Y.L., "The potentials at the junctions of monovalent chloride solutions," (1921) *J. Am. Chem. Soc.* 43:2563-2573.

MacInnes, D.A., "Liquid junction potentials," (1915) *J. Am. Chem. Soc.* 37:2301-2307.

Mahato, R.I. "Non-viral peptide-based approaches to gene delivery," (1999) *Journal of Drug Targeting* 7(4):249-268.

McDonald, J.C. et al., "Fabrication of microfluidic systems in poly(dimethylsiloxane)," (Jan. 2000) *Electrophoresis*, 21:27-40.

Meyer, F. and M. Finer, "Gene therapy: progress and challenges," (Dec. 2001) *Cellular and Molecular Biology* 47(8):1277-1294.

Munson, M.S. et al., "Passive electrophoresis in microchannels using liquid junction potentials," (Aug. 2002) *Electrophoresis* 23:2642-2652.

Pichon, C. et al., "Histidine-rich peptides and polymers for nucleic acids delivery," (Dec. 2001) *Advanced Drug Delivery Reviews* 53:75-94.

Roberts, E.J. and Fenwick, F., "A simple type of flowing junction," (1927) *J. Am. Chem. Soc.* 49:2787-2791.

Samson, E. and Marchand, J., "Numerical solution of the extended Nernst-Planck model," (1999) *J. Colloid Interface Sci.* 215:1-8.

Segura, T. and L.D. Shea, "Materials for non-viral gene delivery," (Aug. 2001) *Annual Review of Materials Research* 31:25-46.

Shoji, S., "Fluids for sensor systems," (1998) *Topics in Current Chemistry*, 194:163-188.

Skryll, Yu., "The effects of hyperbolic diffusion in liquid junctions," (Apr. 2000) *Phys. Chem. Chem .Phys.* 2:2969-2976.

Tang, M.X. and F.C. Szoka, "The influence of polymer structure on the interactions of cationic polymers with DNA and morphology of the resulting complexes," (1997) *Gene Therapy* 4:823-832.

Taylor, P.B., "Electromotive force of the cell with transference and theory of interdiffusion of electrolytes," (1927) *J. Phys. Chem.* 31:1478-1500.

Templeton, N.S., "Cationic liposome-mediated gene delivery *in vivo*," (Apr. 2002) *Bioscience Reports* 22(2):283-295.

Turunen, M.P. et al., Efficient adventitial gene delivery to rabbit carotid artery with cationic polymer-plasmid complexes, (1999) *Gene Therapy* 6:6-11.

Vazquez, M. et al., D., "Electrophoretic injection within microdevices," (May 2002) *Anal. Chem.* 74:1952-1961.

Verpoorte, E., "Microfluidic chips for clinical and forensic analysis," (Mar. 2002) *Electrophoresis* 23:677-712.

Wang, J., "On-chip enzymatic assays," (Mar. 2002) *Electrophoresis* 23:713-718.

Weigl, B.H. and P. Yager, "Microfluidic diffusion-based separation and detection," (1999) *Science* 283(5400), 346-347.

\* cited by examiner

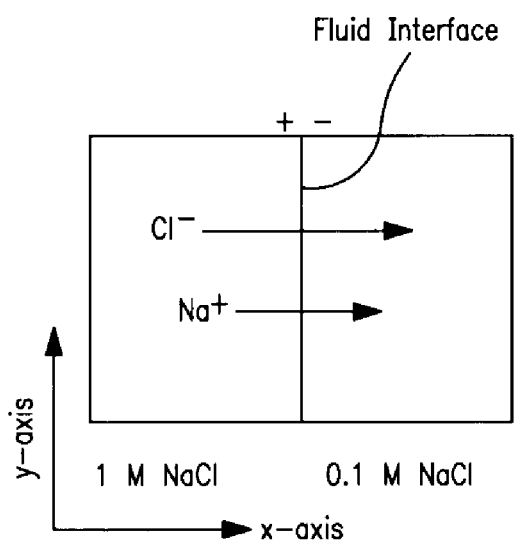
FIG. IA
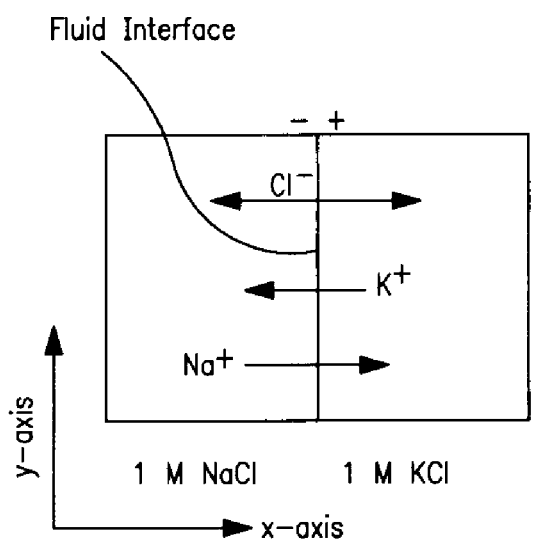
FIG. IB

USE OF LIQUID JUNCTION POTENTIALS FOR ELECTROPHORESIS WITHOUT APPLIED VOLTAGE IN A MICROFLUIDIC CHANNEL

CROSS REFERENCE TO RELATED APPLICATIONS

This application claims priority to U.S. provisional application Ser. No. 60/328,328 filed Oct. 9, 2001, which is hereby incorporated by reference in its entirety to the extent not inconsistent with the disclosure herewith.

SOURCES OF GOVERNMENT FUNDING

This work was funded, in part, by the U.S. Government. The U.S. Government may have some rights to certain aspects of the invention disclosed herein.

BACKGROUND OF THE INVENTION

Control and manipulation of charged particles in microfluidic systems is very useful for such applications as sample preconditioning (removal of interfering substances), electrophoretic separation (fractionation) of charged particles, enhanced or delayed mixing across a fluid interface, focusing particles in a fluid stream in one or two dimensions, and concentration of charged reactants at a fluid interface.

Microfluidic systems and methods of use have been described in detail (Verpoorte, E., Electrophoresis, 2002 23(5), 677–712; Lichtenberg, J., et al., Talanta, 2002.56(2), 233–266; Beebe, D. J., et al., Annual Review of Biomedical Engineering, 2002,4, 261–286; Wang, J., Electrophoresis, 2002, 23(5), 713–718; Becker, H. and L. E. Locascio, Talanta, 2002, 56(2), 267–287; Chovan, T. and A. Guttman, Trends in Biotechnology, 2002.20(3), 116–122; Becker, H. and C. Gartner, Electrophoresis, 2000, 21(1), 12–26; McDonald, J. C., et al., Electrophoresis, 2000, 21(1), 27–40; Weigl, B. H. and P. Yager, Science, 1999, 283(5400), 346–347; and Shoji, S., *Microsystem Technology in Chemistry and Life Science*, 1998, 163–188.) The behavior of fluids under laminar flow, a hallmark of microfluidic technologies, allows contacting of two miscible fluids in a microchannel such that mixing only occurs through diffusive transport, which may be augmented by an imposed field, as in the H-filter (Brody, J. P., et al., Biophys J 1996, 71, 3430–3441; Weigl, B. H., et al., Science 1999, 283, 346–347) and T-sensor (Kamholz, A. E., et al., Anal Chem 1999, 71, 5340–5347; Kamholz, A. E., et al., Biophys J 2001, 80, 155–160; Kamholz, A. E., et al., Biophys J 2001, 80, 1967–1972).

Methods for controlling the flow (transport) of particles in microfluidic systems have also been described, and include the use of electrophoresis, transverse electrophoresis, and hydrodynamic focusing, among others.

Flow cytometry, or the analysis of individual particles in a fluid, requires the single-file alignment of the particles in an analysis region. Flow cytometers in microfluidic systems rely on the use of sheath fluids to hydrodynamically focus particles in a stream.

Transverse electrophoresis requires the application of an external electric field across a microchannel to drive electrophoretic transport across the microchannel, and effectively separate charged species contained in the fluids in the microchannel. While effective, microfluidic electrophoresis adds complexity to the design of a microfluidic device by requiring additional fabrication techniques and steps for the incorporation of metal electrodes into the microfluidic channel. In addition, a microfluidic device incorporating traditional techniques of transverse electrophoresis requires an external voltage source.

The formation of an electrical potential at the interface of two fluids that have different ionic compositions, the liquid junction potential (LJP), is a phenomenon that has been well studied experimentally and theoretically since the late 1800's (MacInnes, D. A., *The Principles of Electrochemistry*, Reinhold Publishing, New York 1939; Planck, M., Ann. Phys. Chem. 1890, 40, 561–576; Jahn, H., Z. Phys. Chem. 1900, 33, 545–576; Henderson, P., Z. Phys. Chem. 1907, 59, 118–127; Henderson, P., Z. Phys. Chem. 1908, 63, 325–345; Lewis, G. N., Sargent, L. W., J. Am. Chem. Soc. 1909, 31, 363–367.; MacInnes, D. A., J. Am. Chem. Soc. 1915, 37, 2301–2307; Lamb, A. B., et al., J. Am. Chem. Soc. 1920, 42, 229–237; MacInnes, D. A., et al., J. Am. Chem. Soc. 1921, 43, 2563–2573; Harned, H. S., J. Phys. Chem. 1926, 30, 433–456; Roberts, E. J., et al., J. Am. Chem. Soc. 1927, 49, 2787–2791; Taylor, P. B., J. Phys. Chem. 1927, 31, 1478–1500; Guggenheim, E. A., J. Phys. Chem. 1929, 33, 842–849; Guggenheim, E. A., J. Am. Chem. Soc. 1930, 52, 1315–1337; Christiansen, T. F., IEEE Trans. Biomed. Eng. 1986, 33, 79–82; Forland, K. S., et al., J. Stat. Phys. 1995, 78, 513–529.) Methods of predicting the magnitude of the liquid junction potential as well as ways to compensate for it have been developed (MacInnes, 1939; MacInnes, 1921; Guggenheim, 1929; Guggenheim, 1930; Cobben, P. L. et al., Anal Chim Acta 1993, 276, 347–352; Lvov, S. N., et al., J Electroanal Chem 1996, 403, 25–30; Borge, G., et al., J Electroanal Chem 1997, 440,183–192). Detailed mathematical analysis and modeling of the underlying phenomena have also been pursued (Henry, J., et al., Asymptotic Anal 1995, 10, 279–302; Skryll, Yu., PCCP Phys Chem Chem Phys 2000, 2, 2969–2976; Samson, E., et al., J Colloid Interface Sci 1999, 215, 1–8). When an electrolyte, or ion concentration gradient exists between fluids flowing in adjacent laminar flow in a microfluidic channel, differential rates of diffusion of the ionic species can lead to a microscopic separation of charge, generating an electric potential. This potential is referred to as the liquid junction potential. This effect has been studied extensively in the presence of a selective barrier between two fluid phases, which often serves to accentuate the differences in transport of the chemical species. Although its effects often go overlooked (Demas, J. N., et al., Appl Spectrosc 1998, 52, 755–762; Greenlee, R. D., et al., Biotechnol Prog 1998,14, 300–309), the LJP could cause significant problems in many microfluidic systems by inducing spurious electrophoretic transport of analytes.

Borge (Borge, G., et al., J Electroanal Chem 1997, 440, 183–192) discloses the use of LJP for the potentiometric measurement of equilibrium constants of systems displaying acid/base equilibrium. Beyond this application, the LJP has not to date been exploited as a tool due to its relatively low magnitude and the short distances over which it acts.

All references cited herein are incorporated in their entirety to the extent not inconsistent herewith.

SUMMARY OF THE INVENTION

The present invention provides for a liquid junction potential (LJP) device useful in microfluidic devices for particle transport control to effect electrophoretic separation (fractionation), particle focusing, acceleration and deceleration of mixing, and concentration of reactants, without the application of an external electrical potential. Methods for the use of such a device are also provided.

The LJP will almost always exist at the interface of two fluids in adjacent laminar flow if the two fluids have different ionic compositions. The potential can be generated at the interface between two solutions having different ionic concentrations, for example, or at the interface between solutions containing equivalent electrolyte concentrations of different ionic species. The junction potential is generated by the differences in mobility between the ionic species when the fluids have different ionic concentrations. For almost any electrolyte there will be a difference in the mobilities of the positive and negative ions. As the ions diffuse down their concentration gradients, a microscopic separation of charge is formed, which creates the LJP.

For solutions having gradient forming species (e.g. electrolytes) that are different, but having a single ion in common, if the differing ions have different mobilities, these differences may be exploited to create a LJP, even if the ionic concentrations of each fluid are the same.

LJPs, applied to microfluidic technologies, result in novel methods and devices for controlling (accelerating or decelerating) the movement (transport) of charged particles in microfluidic systems. This transport control via the LJP is also referred to as "passive electrophoresis" (PE). Specifically, this invention is directed to microfluidic PE methods for one-dimensional (1D) (a core fluid stream situated between two sheath fluid streams) and two-dimensional (2D) (core fluid surrounded on all sides by sheath fluid) focusing of charged particles in a fluid, extraction of particles from a fluid, electrophoretic separation (fractionation), of charged particles in a fluid, the concentration of reactive particles from two fluid streams at or near the fluid interface, and the acceleration or deceleration of mixing between two or more fluids in a microfluidic device. The invention also provides microfluidic devices incorporating LJP, methods of making such LJP microfluidic devices, and methods of utilizing such devices for the determination of the concentration of charged particles in a fluid.

In one embodiment of this invention, a method is provided for controlling the transport of a charged particle in a first fluid stream with respect to an interface between said first fluid stream and a second fluid stream in adjacent laminar flow therewith in a microfluidic channel, the method comprising creating a liquid junction potential at said interface by providing ions in at least one of said fluids of charge, concentration, mobility, and/or charge magnitude selected to accelerate or decelerate movement of said charged particle with respect to said interface.

A method is also provided wherein charged particles are focused in one dimension within a microfluidic channel, the method comprising the steps of:
 a) introducing a core fluid containing a charged particle into said microfluidic channel; and
 b) introducing sheath fluid into said microfluidic channel such that the sheath fluid surrounds the core fluid on two opposite sides of the core fluid and such that the core fluid and each sheath fluid form a fluid interface and flow in adjacent laminar flow in said microfluidic channel;
  said sheath fluid comprising a first set of gradient-forming species and said core fluid optionally comprising the same gradient-forming species, said gradient-forming species comprising at least a first ion and a second ion, wherein said first ion has a charge opposite the charge of said particle and has a higher mobility than said second ion and wherein said second ion has the same charge as said particle and wherein when said gradient-forming species are present in said core fluid, said first ion is present in higher concentration in said sheath fluid than in the core fluid;
  whereby a liquid junction potential is formed at each interface between said sheath fluids and said core fluid and charged particles are focused in said core fluid.

Alternatively said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

A method is also provided wherein charged particles are extracted from a fluid within a microfluidic channel, the method comprising the steps of:
 a) introducing a core fluid containing a first charged particle into said microfluidic channel; and
 b) introducing sheath fluid into said microfluidic channel such that the sheath fluid surrounds the core fluid on two opposite sides of the core fluid and a fluid interface is formed between the core fluid and each sheath fluid and said core and sheath fluids flow in adjacent laminar flow in said microfluidic channel;
  wherein said sheath fluid comprises a first set of gradient-forming species and said core fluid optionally comprises the same set of gradient-forming species, said set of gradient-forming species comprising at least a first ion and a second ion, wherein said first ion has the same charge of said particle and has a higher mobility than said second ion and wherein said second ion has the opposite charge of said particle and wherein when said gradient-forming species are present in said core fluid said first ion is present in higher concentration in the sheath fluid than in the core fluid;
  whereby a liquid junction potential is formed at each interface between said sheath fluids and said core fluid and said charged particles are extracted from said core fluid.

Alternatively said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

A method is also provided wherein charged particles are separated within a microfluidic channel, the method comprising the steps of:
 a) introducing a core fluid containing at least a first and a second charged particle into said microfluidic channel, wherein each of said charged particles has the same charge and each of said charged particles has a different mobility; and
 b) introducing sheath fluid into said microfluidic channel such that the sheath fluid surrounds the core fluid on two opposite sides of the core fluid and a fluid interface is formed between the core fluid and each sheath fluid and said core fluid and said sheath fluids flow in adjacent laminar flow in said microfluidic channel;
  wherein said sheath fluid comprises a first set of gradient-forming species and said core fluid optionally comprises the same set of gradient-forming species, said set of gradient-forming species comprising at least a first ion and a second ion, wherein said first ion has the same charge of said charged particles and has a higher mobility than said second ion and wherein said second ion has the opposite charge of said particle and wherein when said gradient-forming species are present in said core fluid said first ion is present in higher concentration in the sheath fluid than in the core fluid;

whereby a liquid junction potential is formed at each interface between said sheath fluid and said core fluid and said charged particles are separated.

Alternatively said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

A method is also provided wherein charged particles of opposite charge are extracted and separated from a fluid within a microfluidic channel, the method comprising the steps of:

a) introducing a core fluid containing at least first and second charged particles of opposite charge into said microfluidic channel, said core fluid comprising a set of core gradient-forming species comprising at least first and second ions; and b) introducing a first sheath fluid into said microfluidic channel to form a fluid interface with said core fluid, said first sheath fluid comprising a first set of sheath gradient-forming species that are the same as the set of core gradient-forming species and wherein the ionic concentration of the first sheath fluid is higher than the ionic concentration of said core fluid and said first sheath fluid is in adjacent laminar flow with said core fluid in said microfluidic channel;

c) introducing a second sheath fluid into said microfluidic channel to form a fluid interface with said core fluid, said second sheath fluid optionally comprising a second set of sheath gradient-forming species that is the same as the set of core gradient-forming species and wherein when the second sheath fluid comprises the second set of sheath gradient-forming species, said second sheath fluid has a lower ionic concentration than the ionic concentration of said core fluid and said second sheath fluid is in adjacent laminar flow with said core fluid in said microfluidic channel;

said sets of gradient-forming species comprising at least a first ion and a second ion, wherein said first ion has the same charge of said first charged particle and has a higher mobility than said second ion and wherein said second ion has the same charge of said second particle;

whereby a liquid junction potential is formed at each fluid interface between said sheath fluids and said core fluid and said oppositely charged particles are separated and extracted from said core fluid.

Alternatively the ionic concentrations of all of the sets of gradient-forming species are equal and said set of core gradient-forming species is different than said first set of sheath gradient-forming species;

said second set of sheath gradient-forming species is different from said core gradient-forming species and said first set of sheath gradient-forming species;

said first ion in said first set of sheath gradient-forming species has higher mobility than said first ion in said core gradient-forming species;

said first ion in said core gradient-forming species has higher mobility than said first ion in said second set of sheath gradient-forming species; and the second ion in each set of gradient-forming species is the same.

A method is also provided wherein charged particles are focused in two dimensions within a microfluidic channel, the method comprising the steps of:

a) introducing a core fluid containing a charged particle into said microfluidic channel; and b) introducing a sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel;

wherein said sheath fluid comprises a first set of gradient-forming species and said core fluid optionally comprises the same set of gradient-forming species, said set of gradient-forming species comprising at least a first ion and a second ion, wherein said first ion has a charge opposite the charge said charged particle and has a higher mobility than said second ion and wherein said second ion has the same charge as said particle and wherein when said gradient forming species are present in said core fluid, said first ion is present in higher concentration in the sheath fluid than in the core fluid;

whereby a liquid junction potential is formed at the interface between said sheath fluid and said core fluid and said charged particles are focused within said core fluid.

Alternatively said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

A method is also provided wherein charged particles are extracted from a fluid stream within a microfluidic channel, the method comprising the steps of:

a) introducing a core fluid containing a charged particle into said microfluidic channel; and b) introducing sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel wherein said sheath fluid comprises a first set of gradient-forming species and said core fluid optionally comprises the same set of gradient-forming species, said set of gradient-forming species comprising at least a first ion and a second ion, wherein said first ion has the same charge as said charged particle and has a higher mobility than said second ion and wherein said second ion has the opposite charge of said charged particle and wherein when said gradient forming species are present in said core fluid, said first ion is present in higher concentration in the sheath fluid than in the core fluid;

whereby a liquid junction potential is formed at the interface between said sheath fluid and said core fluid and said charged particles are extracted from said core fluid.

Alternatively, said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

A method is also provided wherein charged particles are focused in two dimensions within a microfluidic channel, the method comprising the steps of:
  a) introducing a core fluid containing a charged particle into said microfluidic channel; and
  b) introducing sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel
    wherein said core fluid comprises a first set of gradient-forming species and said sheath fluid optionally comprises the same gradient-forming species, said set of gradient-forming species comprising at least a first ion and a second ion, wherein said first ion has the opposite charge of said charged particle and has a lower mobility than said second ion and wherein said second ion has the same charge as said charged particle and wherein when said gradient forming species are present in said sheath fluid, said ions are present in higher concentration in the core fluid than in the sheath fluid;
    whereby a liquid junction potential is formed at the interface between said sheath fluid and said core fluid and said charged particles are focused in said core fluid.

Alternatively said sheath fluid comprises a second set of gradient-forming species wherein the ionic concentrations of the first and second sets of gradient-forming species are equal, the second ion in each set of gradient-forming species is the same, and the first ion in the second set of gradient-forming species has a higher mobility than the first ion in the first set of gradient-forming species.

A method is also provided wherein charged particles are extracted from a fluid stream within a microfluidic channel, the method comprising the steps of:
  a) introducing a core fluid containing a charged particle into said microfluidic channel; and
  b) introducing sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel
    wherein said core fluid comprises a first set of gradient-forming species and said sheath fluid optionally comprises the same gradient-forming species, said set of gradient-forming species comprising at least a first ion and a second ion, wherein said first ion has the same charge as said charged particle and has a lower mobility than said second ion and wherein said second ion has the opposite charge of said charged particle and wherein when said gradient forming species are present in said sheath fluid said first ion is present in higher concentration in said core fluid than in said sheath fluid;
    whereby a liquid junction potential is formed at the interface between said sheath fluid and said core fluid and said charged particles are extracted from said core fluid.

Alternatively said sheath fluid comprises a second set of gradient-forming species wherein the ionic concentrations of the first and second sets of gradient-forming species are equal, the first ion in each set of gradient-forming species is the same, and the second ion in the first set of gradient-forming species has a higher mobility than the second ion in the first set of gradient-forming species.

A method is also provided wherein the mixing of charged particles is accelerated between two or more fluids within a microfluidic channel, the method comprising the steps of:
  a) introducing a first fluid containing a negatively charged particle into said microfluidic channel; and
  b) introducing at least a second fluid into said microfluidic channel such that a fluid interface is formed between the first fluid and the second fluid and the first fluid and the second fluid flow in adjacent laminar flow in said microfluidic channel
    wherein said first fluid comprises a set of gradient-forming species and said second fluid optionally comprises the same set of gradient-forming species, said set of gradient-forming species comprising a cation and an anion, wherein said cation has a higher mobility than said anion and wherein when said gradient forming species are present in said second fluid, said ions are present in lower concentration in said second fluid than in said first fluid;
    whereby a liquid junction potential is formed at the interface between said first fluid and said second fluid and the mixing of said negatively-charged particles into said second fluid is accelerated.

Alternatively said second fluid comprises a second set of gradient-forming species wherein the ionic concentrations of the first and second sets of gradient-forming species are equal, the anion in each set of gradient-forming species is the same, and the cation in the first set of gradient-forming species has a higher mobility than the cation in the second set of gradient-forming species.

Alternatively said second fluid comprises a second set of gradient-forming species wherein the ionic concentrations of the first and second sets of gradient-forming species are equal, the cation in each set of gradient-forming species is the same, and the anion in the second set of gradient-forming species has a higher mobility than the anion in the first set of gradient-forming species.

A method is also provided wherein the mixing of charged particles is decelerated between two or more fluids within a microfluidic channel, the method comprising the steps of:
  a) introducing a first fluid containing a positively charged particle into said microfluidic channel; and
  b) introducing at least a second fluid into said microfluidic channel such that a fluid interface is formed between the first fluid and the second fluid and the first fluid and the second fluid flow in adjacent laminar flow in said microfluidic channel
    wherein said first fluid comprises a set of gradient-forming species and said second fluid optionally comprises the same set of gradient-forming species, said set of gradient-forming species comprising a cation and an anion, wherein said cation has a higher mobility than said anion and wherein when said gradient forming species are present in said second fluid said ions are present in higher concentration in said first fluid than in said second fluid;

whereby a liquid junction potential is formed at the interface between said sheath fluid and said core fluid and said mixing of said positively-charged particles into said second fluid is decelerated.

Alternatively said second fluid comprises a second set of gradient-forming species wherein the ionic concentrations of the first and second sets of gradient-forming species are equal, the anion in each set of gradient-forming species is the same, and the cation in the first set of gradient-forming species has a higher mobility than the cation in the second set of gradient-forming species.

Alternatively said second fluid comprises a second set of gradient-forming species wherein the ionic concentrations of the first and second sets of gradient-forming species are equal, the cation in each set of gradient-forming species is the same, and the anion in the second set of gradient-forming species has a higher mobility than the anion in the first set of gradient-forming species.

A method is also provided wherein the mixing of charged particles is accelerated between two or more fluids within a microfluidic channel, the method comprising the steps of:
a) introducing a first fluid containing a positively charged particle into said microfluidic channel; and
b) introducing at least a second fluid into said microfluidic channel such that a fluid interface is formed between the first fluid and the second fluid and the first fluid and the second fluid flow in adjacent laminar flow in said microfluidic channel
   wherein said second fluid comprises a set of gradient-forming species and said first fluid optionally comprises the same set of gradient-forming species, said set of gradient-forming species comprising a cation and an anion, wherein said cation has a higher mobility than said anion and wherein when said gradient forming species are present in said first fluid said ions are present in higher concentration in said second fluid than in said first fluid;
   whereby a liquid junction potential is formed at the interface between said first and second fluids and the mixing of said positively-charged particle into said second fluid is accelerated.

Alternatively said first fluid comprises a second set of gradient-forming species wherein the ionic concentrations of the first and second sets of gradient-forming species are equal, the cation in each fluid is the same, and the anion in the first fluid has a higher mobility than the anion in the second fluid.

Alternatively said first fluid comprises a second set of gradient-forming species wherein the ionic concentrations of the first and second sets of gradient-forming species are equal, the anion in each set of gradient-forming species is the same, and the cation in the second set of gradient-forming species has a higher mobility than the cation in the first set of gradient-forming species.

A method is also provided wherein the mixing of charged particles is decelerated between two or more fluids within a microfluidic channel, the method comprising the steps of:
a) introducing a first fluid containing a negatively charged particle into said microfluidic channel; and
b) introducing at least a second fluid into said microfluidic channel such that a fluid interface is formed between the first fluid and the second fluid and the first fluid and the second fluid flow in adjacent laminar flow in said microfluidic channel
   wherein said second fluid comprises a set of gradient-forming species and said first fluid optionally comprises the same set of gradient-forming species, said set of gradient-forming species comprising a cation and an anion, wherein said cation has a higher mobility than said anion and wherein when said gradient forming species are present in said first fluid said ions are present in higher concentration in said second fluid than in said first fluid;
   whereby a liquid junction potential is formed at the interface between said first fluid and said second fluid and said mixing of said negatively-charged particles into said second fluid is decelerated.

Alternatively said first fluid comprises a second set of gradient-forming species wherein the ionic concentrations of the first and second sets of gradient-forming species are equal, the cation in each fluid is the same, and the anion in the first fluid has a higher mobility than the anion in the second fluid.

Alternatively said first fluid comprises a second set of gradient-forming species wherein the ionic concentrations of the first and second sets of gradient-forming species are equal, the anion in fluid is the same, and the cation in the second fluid has a higher mobility than the cation in the first fluid.

A method is also provided wherein the rate of a reaction in a microfluidic channel is enhanced, the method comprising the steps of:
a) introducing a first fluid containing a first reactive charged particle into said microfluidic channel;
b) introducing a second fluid containing a second reactive charged particle into said microfluidic channel such that a fluid interface is formed between said first and second fluids and said first and second fluids are in adjacent laminar flow within said microfluidic channel;
   wherein:
   said first reactive particle has the opposite charge of said second reactive particle;
   said second fluid comprises a set of gradient-forming species;
   said first fluid optionally comprises the same set of gradient-forming species;
   said set of gradient-forming species comprising a first ion and a second ion wherein
   said first ion has a charge opposite the charge of said second reactive charged particle and of said second ion and has a higher mobility than said second ion;
   and when said gradient forming species are present in said first fluid said ions are present in higher concentration in said second fluid than in said first fluid;
   whereby a liquid junction potential is formed at said interface between said first and second fluids and the reaction of said oppositely-charged particles is enhanced.

Alternatively said first fluid comprises a second set of gradient-forming species wherein the ionic concentrations of the first and second sets of gradient-forming species are equal, the second ion in each fluid is the same, and the first ion in the second fluid has a higher mobility than the first ion in the first fluid.

This invention also provides a microfluidic device comprising:
a microfluidic channel containing:
   a) at least a first and a second fluid stream in parallel laminar flow in said microfluidic channel to form at least one fluid interface;

b) charged particles contained in at least one of said fluid streams;

c) ions contained in at least one of said fluid streams of a charge, concentration, mobility and/or charge magnitude selected to control movement of said charged particles with respect to said interface.

This invention also provides a method of making a microfluidic device for establishing a liquid junction potential, said method comprising:

a) providing a microfluidic channel in said device;

b) flowing into said microfluidic channel at least a first and a second fluid stream in parallel laminar flow in said microfluidic channel to form at least one fluid interface;

c) providing charged particles contained in at least one of said fluid streams;

d) providing ions contained in at least one of said fluid streams of a charge, concentration, mobility and/or charge magnitude selected to control movement of said charged particles with respect to said interface.

This invention further provides a method for determining the concentration of charged particles in a first fluid in laminar flow with a second fluid in a microchannel by a method based on correlating the rate of diffusion of said charged particles across an interface between said first and second fluids with the concentration of said charged particles, the method comprising determining the concentration of charged particles in said fluid by:

a) measuring the rate of diffusion of said charged particles across said interface or the position of said particles with respect to said interface to obtain a first diffusion value;

b) determining the presence of an electric potential across said interface;

c) calculating the effect of said electric potential on said rate of diffusion to obtain a correction value;

d) adjusting said first diffusion value by said correction value to obtain a second diffusion value;

e) correlating said second diffusion value with the concentration of said charged particles.

In all of the embodiments of this invention, the fluid interfaces formed may be linear or non-linear.

A microfluidic channel is a channel having at least one dimension less than 1 mm. When flow between two or more fluids in a microfluidic channel is laminar, flow is non-turbulent and mixing between the adjacent fluids flowing within the channel is by diffusion only. This lack of convective mixing defines the flow as "laminar". An exemplary microfluidic channel is shown in FIG. 2, although it is important to note that the methods of this invention can be used in any microfluidic channel in which two or more fluids are in adjacent laminar flow. The flow direction in such a microfluidic channel is defined herein as being along the z axis as shown in FIG. 2, and when two or more streams are in "parallel (adjacent) laminar flow", the diffusion dimension between the streams is along the x axis as shown in FIG. 2. In the microfluidic channels described in this invention, w, the remaining dimension, can be either less than or greater than d.

The term "adjacent" flow is not limited to microchannels in which the interface between the two fluids is a straight line. The interface may be 'jagged' or 'wavy' for example, to increase the area of the interface between the two fluids. Or, for instance, a first fluid may be surrounded on all sides (two-dimensionally) by sheath fluid such that the flow is co-axial (the streams have circular cross-sections rather than rectangular, for example). In such two-dimensional systems, the core fluid may also take any shape that increases the area of the interface between the two fluids.

The term "particle" as used herein refers to a particulate material including molecules, cells, polymers, microspheres, suspended and dissolved particles, nanoparticles, proteins, ions and atoms of organic or inorganic composition. "Charged particles" of interest herein, i.e., the particles whose transport is effected by the methods of this invention, are particles that, in a given fluid, buffer, or electrolyte, have a net electrical charge. Particles that normally carry no charge can be made positive or negative by choosing an appropriate buffer or electrolyte. A charge, or a charged particle, can be either negative or positive. The term "same charge" is used herein to indicate that two species are either both positive or both negative and is not used to indicate the magnitude of the charge (e.g. +2 or +1).

The term "gradient-forming species" as used herein refers to ionic particles having positive or negative charge (cationic or anionic, respectively) in solution that are capable of forming a LJP across a fluid interface in a microchannel. Gradient-forming species do not include the charged particles of interest whose transport is effected by the LJP. The fluids forming the interface may have different concentrations of the same gradient-forming species to form a concentration gradient upon formation of a fluid interface, or they may have equal total ion concentrations, but differing cations or anions that have different diffusivities. Examples of gradient-forming species include electrolytes in an electrolytic solution, buffer components, charged polymers, and the like. A "set of gradient-forming species" refers to the set of gradient-forming species initially present in a fluid before formation of a fluid interface with one or more other fluids, and comprises positive and negative ions (cations and anions, respectively).

"Accelerated" and "decelerated" as in "accelerated transport" or "decelerated transport" are terms used to describe a change in the rate of transport of a charged particle of interest between fluids relative to the rate of transport that would occur by diffusion only if no LJP were present. It is possible that the effect of the LJP could be so large as to overwhelm diffusion completely, and cause net particle movement up a concentration gradient.

An electrolyte is a solution that conducts electrical current and supports ionized species, e.g. cations (positive charge) and anions (negative charge). The cations and anions of electrolytes are one example of gradient-forming species.

The term "mobility" as it relates to charged particles or ions is used to describe an ion's rate of transport within an electric field. Mobility of an ionic species is proportional to its diffusivity (D) times its charge magnitude (C). Diffusivity, in turn, is inversely proportional to the friction coefficient of the molecule in solution, which is a function of the size of the hydration sphere of the ion or particle and its shape.

A "core fluid", as used herein is a fluid that contains charged particles of interest. A "sheath fluid" is a fluid that surrounds a core fluid on at least two sides.

BRIEF DESCRIPTION OF THE DRAWINGS

FIG. 1 illustrates the origin of the liquid junction potential between fluids shown to the right and left of a fluid interface. The arrows represent the diffusive flux of each species, with length corresponding to magnitude. A) A concentration gradient of the sample electrolyte NaCl exists across the x-direction, i.e., initially the fluid on the right does not contain NaCl. The net flux of both the $Na^+$ and $Cl^-$ will lead to a separation in charge creating a potential. B) Liquid junction potentials can also be generated at the interface of two solutions with the same ionic strength, but comprising different ions. In this case the fluid on the left initially contains NaCl and the fluid on the right initially contains KCl. There will be no net flux of Cl⁻, but, the diffusion of Na⁺ across the interface will be slightly faster than the diffusion of K⁺, leading to a separation in charge and therefore a potential.

DETAILED DESCRIPTION OF THE INVENTION

The methods and devices of this invention exploit liquid junction potentials (LJPs) to control the movement of charged particles in microfluidic channels.

Figure 2A:
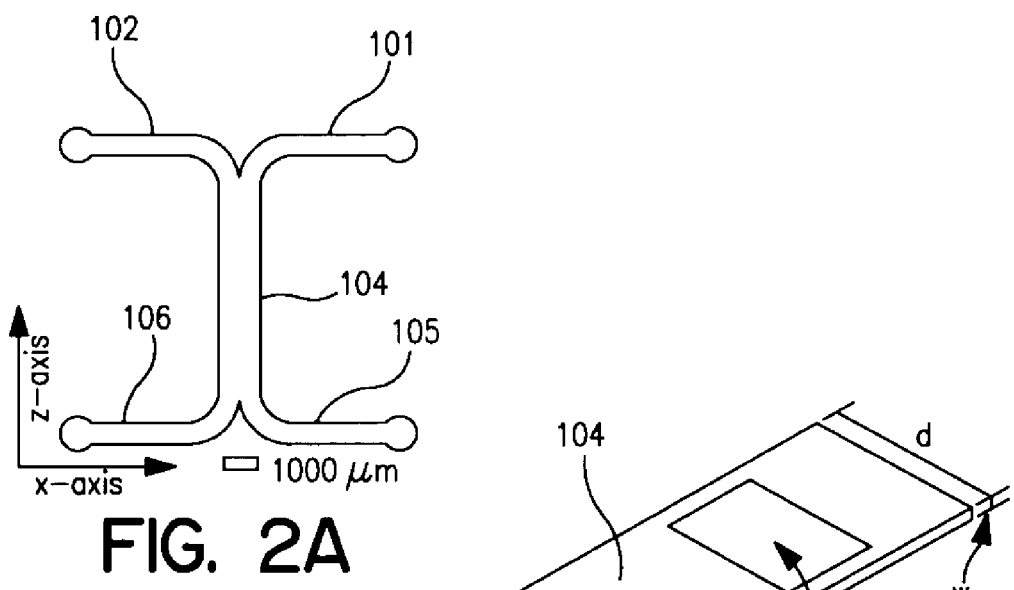
FIG. 2 illustrates an H-Filter flow cell. A) A scale drawing of the entire flow cell is shown. The device is held in a custom-designed manifold to provide fluidic interconnection to the inlets. B) A schematic drawing of just the inlet and main channel sections of the device of A is shown.

The methods and devices described herein utilize microfluidic channels. An exemplary microfluidic channel is the H-filter shown in FIG. 2A. An H-filter is an H-shaped microchannel used to extract species from one stream into another based on their diffusion coefficients. It has two inlets (101 and 102) that feed fluids into a single microfluidic channel (104). Window 103 (FIG. 2B) allows optical measurements to be taken of the fluids in the channel. Exit channels 105 and 106 allow the fluid in the microchannel to be split into two streams. It is important to note that any microfluidic device comprising a microfluidic channel in which two or more fluids are in adjacent laminar flow may be used with the methods of this invention. While the examples and modeling described herein utilize an H-filter, the use of the H-filter is not meant to be limiting, only exemplary.

The small size scale inherent in microfluidic devices allows liquid junction potentials to be used to augment or drive electrophoretic transport, as demonstrated herein. The electrophoretic flux in the experiments described here is generated passively, i.e., without the use of electrodes or the application of an external voltage. This is termed "passive electrophoresis" (PE).

As demonstrated herein, LJPs can be used in numerous applications in which the transport (movement), of charged particles is controlled within a fluid flowing in a microfluidic channel, or across an interface between two fluids flowing in laminar flow in a microfluidic channel. The following examples depict some of these applications to microfluidics, including the deceleration and acceleration of transport of charged particles across a fluid interface, the focusing of charged particles within a fluid, the extraction of charged particles from a fluid, the separation (fractionation) of charged particles from a fluid, and the concentration of charged particles at or near a fluid interface.

There must be a difference in the mobility of ions in two fluids forming a fluid interface to form a LJP. A simple difference in the concentration of an ion pair on either side of the interface satisfies this condition. As an example, consider the liquid interface shown in FIG. 1A. Due to the initial difference in concentration of both $Na^+$ and $Cl^-$ ions between the fluids on the right or the left, both ions will diffuse into the more dilute fluid. However, there is a difference in the diffusivity of the two species and $Na^+$ will initially diffuse more slowly than the $Cl^-$. This induces a separation of charge, which generates an electric field at the fluid interface. Liquid junction potentials can also be generated at the interface of two solutions with the same ionic concentrations, but comprising of different ions. This is illustrated in FIG. 1B in which the left fluid initially contains NaCl and the right fluid initially contains KCl. In this case, because the total ionic concentration is the same for both fluids initially, there will be no net flux of $Cl^-$, but, the diffusion of $Na^+$ will be slightly faster than the diffusion of $K^+$ leading to a separation in charge and therefore a potential across the interface.

Eventually, the LJP electric field slows the flux of charged ions until both cross the boundary at equal rates (Bard and Faulkner, "Electrochemical Methods: Fundamentals and Applications", $2^{nd}$ ed., John Wiley and Sons, New York, 2001, p. 64). The key to the methods and devices of this invention is the exploitation of the LJP before the effects of diffusion override it.

FIGS. 3A–3G depict several embodiments of the present invention in which liquid junction potentials are exploited in a microfluidic system. In all of the embodiments of FIG. 3, fluid flow is into the plane of the paper. Shaded boxes indicate analyte fluids that contain charged particles of interest, i.e. those whose movement it is desired to control. In these examples, the cationic species of the gradient-forming species has a higher mobility (diffuses faster) than the anionic species. The effect on a given charged particle will be directly opposite in systems in which the anionic species has a higher mobility than the cationic species. Solid arrows indicate the direction of the electrophoretic force felt by positively-charged particles of interest near each fluid interface, and dashed arrows represent the direction of the electrophoretic force felt by negatively-charged particles of interest near each fluid interface. The + and − signs indicate the polarity of the charge separation at the interface. The designation "high salt" indicates that the fluid so designated has a higher concentration of gradient-forming species than a fluid with no designation or a fluid designated "medium salt". Similarly, "medium salt" indicates a fluid with a higher concentration of gradient-forming species than one designated "low salt". The term "low salt" may also indicate the initial absence of gradient-forming species. No designation indicates either a lower concentration of gradient-forming species relative to a second fluid, or no gradient-forming species.

Figure 3A:
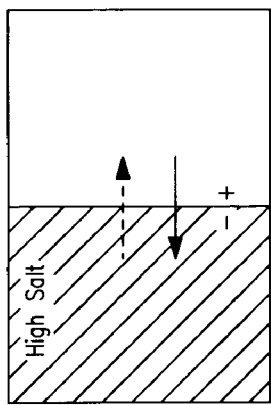
FIG. 3 illustrates numerous embodiments of this invention utilizing LJP. Dashed arrows indicate movement of negatively charged ions. Solid arrows indicate movement of positively-charged ions. The lines between fluids represent fluid interfaces. The + and − at fluid interfaces represent the polarity of the charge separation created by the LJP. The shaded area indicates analyte fluids that contain charged particles of interest. In these embodiments, the cationic species has higher mobility than the anionic species.
- A) Shows a system in which mixing of positively-charged particles of interest would be accelerated across the fluid interface; or negatively-charged particles of interest would be decelerated across the fluid interface.
- B) Shows a system in which negatively-charged particles of interest would be accelerated across the fluid interface; or positively-charged particles of interest would be decelerated across the fluid interface.
- C) Shows a system in which negatively-charged particles of interest would be extracted from the center fluid into the right or left fluids; or positively-charged particles of interest would be focused in the center fluid.
- D) Shows a system in which positively-charged particles of interest would be extracted from the center fluid into the right and left fluids; or negatively-charged particles of interest would be focused in the center fluid.
- E) Shows a system in which particles of interest having positive and negative charges present in the center fluid are separated respectively into the left and right fluids.
- F) Shows a system in which negatively-charged particles of interest in a core fluid surrounded by a sheath fluid would be focused in the core fluid, or positively-charged particle of interest in a core fluid would be extracted into the surrounding sheath fluid in two dimensions.
- G) Shows a system in which positively-charged particles of interest in a core fluid surrounded by a sheath fluid would be focused in the core fluid, or negatively-charged particle of interest in a core fluid would be extracted into the surrounding sheath fluid in two dimensions.
- H) Shows a system in which the oppositely-charged particles of interest polyethylenoimine (PEI) and DNA can be concentrated in a reaction zone near the fluid interface.

FIG. 3A depicts an embodiment of this invention in which a LJP is established to effect either the decelerated transport of negatively-charged particles of interest or the accelerated transport of positively-charged particles of interest across a fluid interface. That is, the faster moving cation (one of the gradient-forming species) diffuses from the area of higher concentration to the area of lower concentration (the fluid containing the particle of interest), faster than the anion diffuses, thereby establishing a LJP at the interface. This results in the transport of positively-charged particles in the analyte fluid across the fluid interface at a rate that is faster than if no LJP existed. In contrast, the transport of any negatively-charged particles in the analyte fluid across the fluid interface will be decelerated relative to the rate in the absence of the LJP.

Figure 3B:
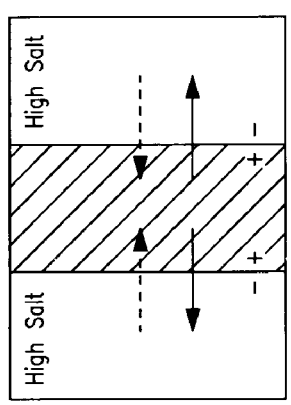

FIG. 3B depicts another embodiment of this invention in which a LJP is established to effect either the decelerated transport of positively-charged particles of interest or the accelerated transport of negatively-charged particles of interest across the fluid interface.

Figure 3C:
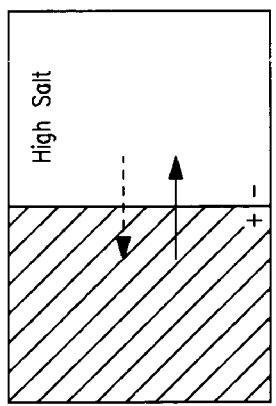
Figure 3D:
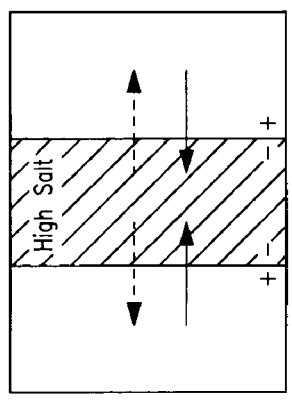
Figure 3E:
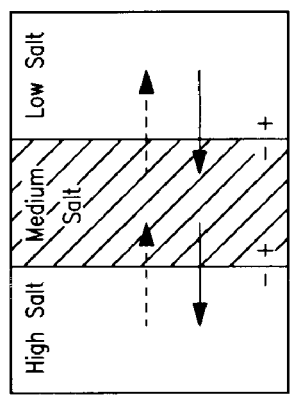

FIG. 3C depicts one embodiment of this invention in which an analyte-containing core fluid stream is flanked by two sheath streams. In this example, the concentration of gradient-forming species is higher in the core stream than in the sheath streams, thereby establishing two LJPs, one at each fluid interface. In such a manner, positively-charged particles of interest in the core fluid are focused in the center of the core fluid, while negatively-charged particles of interest are extracted from the core stream, that is the transport of the negatively-charged particles of interest into the sheath fluids is accelerated relative to their diffusion in the absence of the LJP. FIG. 3E illustrates the opposite configuration, in which the concentration of gradient-forming species is higher in the sheath streams than in the core. As a result, negatively-charged particles of interest in the core fluid are focused in the center of the core fluid, while positively-charged particles of interest are extracted from the core stream.

FIG. 3E illustrates the use of LJP for fractionation of oppositely-charged species from a core analyte fluid. In this example, two LJPs are formed, but with two different charge separation polarities. This creates a situation in which the transport of both the positive and negative particles of interest is accelerated, but in opposite directions, effectively separating (fractionating), the particles according to their charge.

Figure 3G:
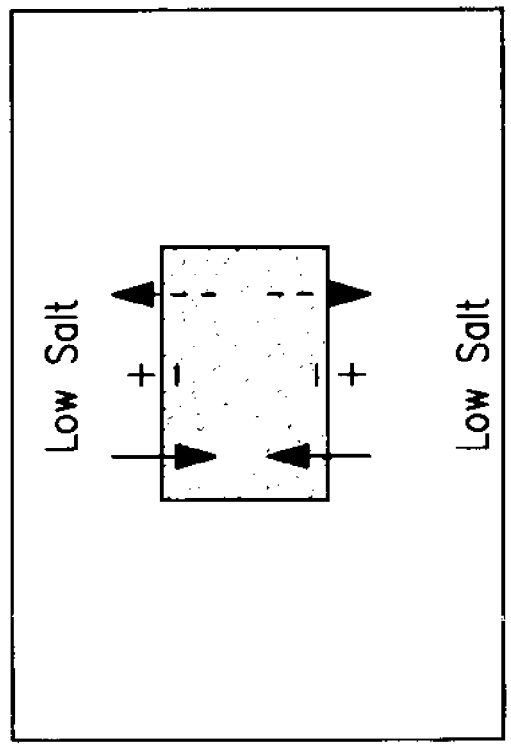
Figure 3F:
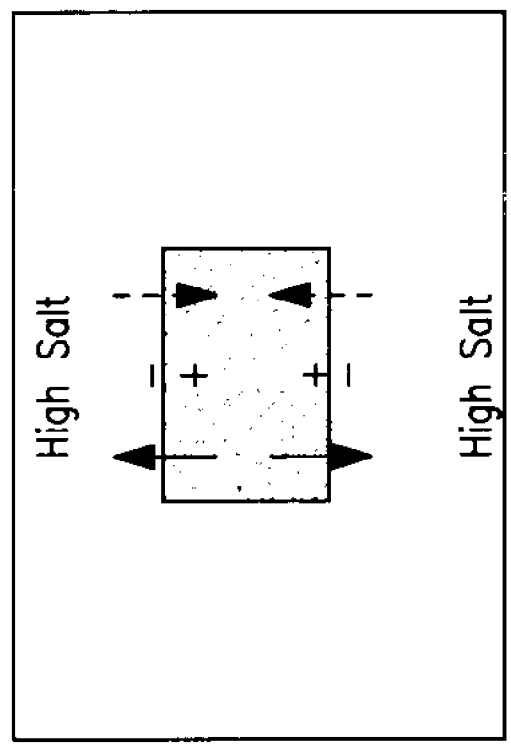

FIGS. 3F and 3G illustrate focusing and extraction, respectively, of charged particles of interest in two dimensions. In these embodiments, a core analyte fluid is 'injected' into a sheath fluid such that the sheath fluid surrounds the analyte fluid on all sides. If the sheath fluid has a higher concentration of gradient-forming species than the analyte fluid (FIG. 3F), and the positively-charged particles in the sheath fluid diffuse across the fluid interface faster than the negatively-charged particles in the sheath fluid, negatively-charged particles in the analyte fluid are focused within the analyte fluid while positively-charged particles are extracted into the sheath fluid. Conversely, if the sheath fluid has a lower concentration of gradient-forming species than the analyte fluid (FIG. 3G), positively-charged particles in the analyte fluid are focused within the analyte fluid while negatively-charged particles are extracted into the sheath fluid.

Figure 3H:
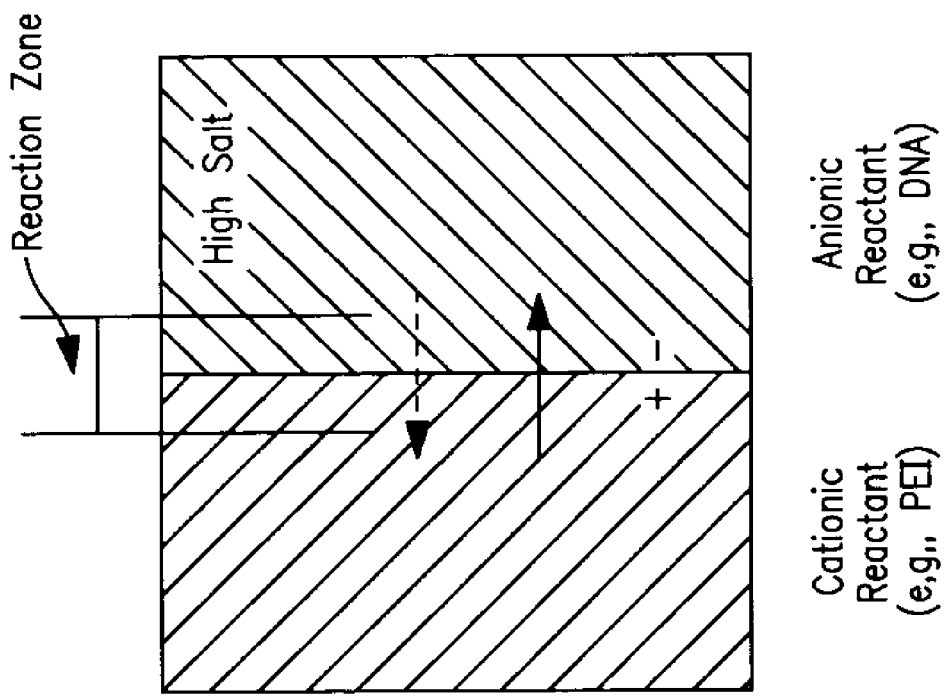

Before two slowly-diffusing chemical species can react with one another they must be brought into close proximity. In a microfluidic channel when two streams are brought into contact in the absence of an applied force, due to laminar flow, the mixing is by interdiffusion of the streams. Because of this, if there are reactants in both streams, the reaction will only occur in the region near the interface where the reactants have interdiffused. The reaction zone will be very small. This will require very long residence times, which implies very slow flow rates or very long channels, both of which can be impractical from a device fabrication and maintenance point of view. However, if one stream had a different ionic content than the other, an LJP would be formed. Because oppositely-charged species will migrate in opposite directions under the same electric field, this can be used to bring oppositely-charged reactants into contact more rapidly than diffusion alone, effectively increasing the size of the reaction zone. This is depicted in FIG. 3H, and further described below.

One example of using the LJP to facilitate reaction of particles in different fluid streams is in the formation of DNA nanoparticles for gene delivery. One method for dramatically increasing the uptake of therapeutic genetic material into a cell, is to create a nanoparticle that contains DNA compacted with an oppositely charged polymer. Much research has been done in this field, and some typical examples of condensing polymers are poly-L-lysine (PLL), polyethyleneimine (PEI), and starburst polyamidoamine (PAMAM) (Templeton, N. S. (2002) *Bioscience Reports* 22(2):283–295; Chan, C. K. and D. A. Jans (2002) "Using nuclear targeting signals to enhance non-viral gene transfer" *Immunology and Cell Biology* 80(2):119–130; De Jesus, O. L. P., et al. (2002) "Polyester dendritic systems for drug delivery applications: In vitro and in vivo evaluation" *Bioconjugate Chemistry* 13(3): 453–461; Davis, M. E. (2002) *Current Opinion in Biotechnology* 13(2):128–131; Meyer, F. and M. Finer (2001) *Cellular and Molecular Biology* 47(8): 1277–1294; Pichon, C. et al. (2001) *Advanced Drug Delivery Reviews* 53(1):75–94; Borchard, G. (2001) *Advanced Drug Delivery Reviews* 52(2):145–150; Segura, T. and L. D. Shea (2001) *Annual Review of Materials Research* 31:25–46; Hennink, W. E., et al. (2001) *Stp Pharma Sciences* 11(1):11–19; De Smedt, S. C., et al. (2000) *Pharmaceutical Research* 17(2):113–126; Mahato, R. I. (1999) *Journal of Drug Targeting* 7(4):249–268; Godbey, W.T., et al. (1999) *Journal of Controlled Release* 60(2–3):149–160; Turunen, M. P., et al. (1999) *Gene Therapy* 6(1):6–11; and Tang, M. X. and F. C. Szoka (1997) *Gene Therapy* 4(8): 823–832). All of these polymers are positively-charged, in contrast to DNA's negative charge. For therapeutically useful applications, the DNA fragments used are typically quite large (on the order of one to ten thousand base pairs which corresponds to a molecular weight range of 600–6,000 kDa). The positively-charged polymers are typically on the order of 25 kDa. Molecules of this size diffuse very slowly. If these reactants were placed next to each other in two different streams in laminar flow in a microfluidic channel, the reaction zone would be very narrow. However, when the salt concentration of one of the streams is raised relative to the other, a junction potential forms. In the case where the cation diffuses faster than the anion, the appropriate configuration is to raise the salt content in the stream that contains the DNA (negatively-charged). The polarization at the interface increases the rate of transport of both reactants towards the center. If the DNA solution had the lower salt content, both reactants would be repelled from the interface. This also is useful, for example, to prevent a reaction from occurring at one interface while a different reaction occurred at another interface. The concentration and identity of the gradient-forming species are chosen such that the LJP has a well-characterized lifetime, after which the transport of the particles in the channel is controlled by diffusion alone. As with all of the examples, if the anion has a higher mobility than the cation, the stream comprising the higher salt concentrations would be reversed as well, i.e., the DNA solution would have the lower salt concentration.

Figure 17A:
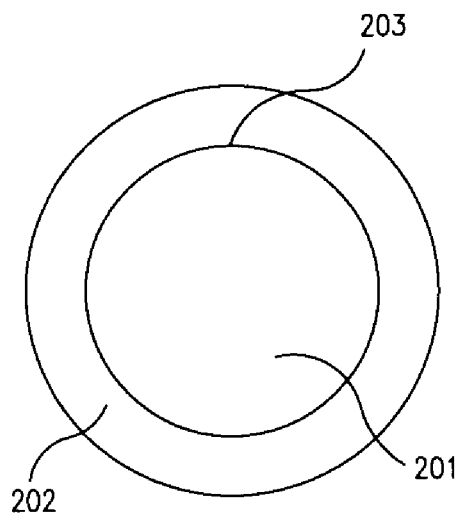
FIGS. 17 A and B depict core fluids of different shapes surrounded by sheath fluids.
FIGS. 17C and D illustrate the formation of non-linear interfaces between adjacent fluid streams. The non-linear interfaces of FIG. 17 are stabilized by LJPs. Fluid flow is into the page.
Figure 17B:
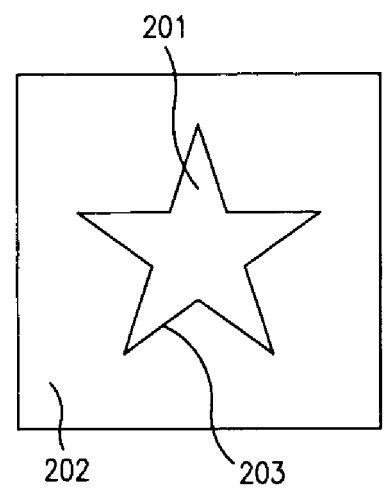
Figure 17C:
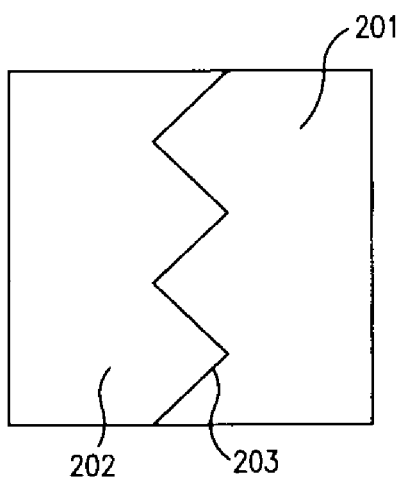
Figure 17D:
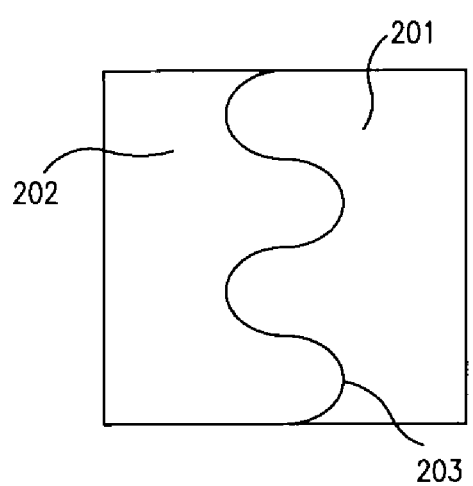

LJPs may also be applied to non-linear fluid interfaces to increase the surface area of the fluid interface to further enhance mixing. Several examples of non-linear interfaces (203) between a first fluid (201) and a second fluid (202) flowing in laminar flow in a microfluidic channel are shown in FIG. 17. FIGS. 17A and 17B depict coaxial sheath flow of two fluids. The non-linear interfaces are initially formed as a result of the shape of the channel used to inject the core fluid into the sheath fluid, and the interfaces are stabilized using LJPs. FIG. 17C illustrates one example of a jagged interface between a core fluid and a sheath fluid. FIG. 17D illustrates a curved interface. FIGS. 17C and 17D show two non-linear interfaces for fluids flowing in rectangular or square microfluidic channels.

Figure 4:
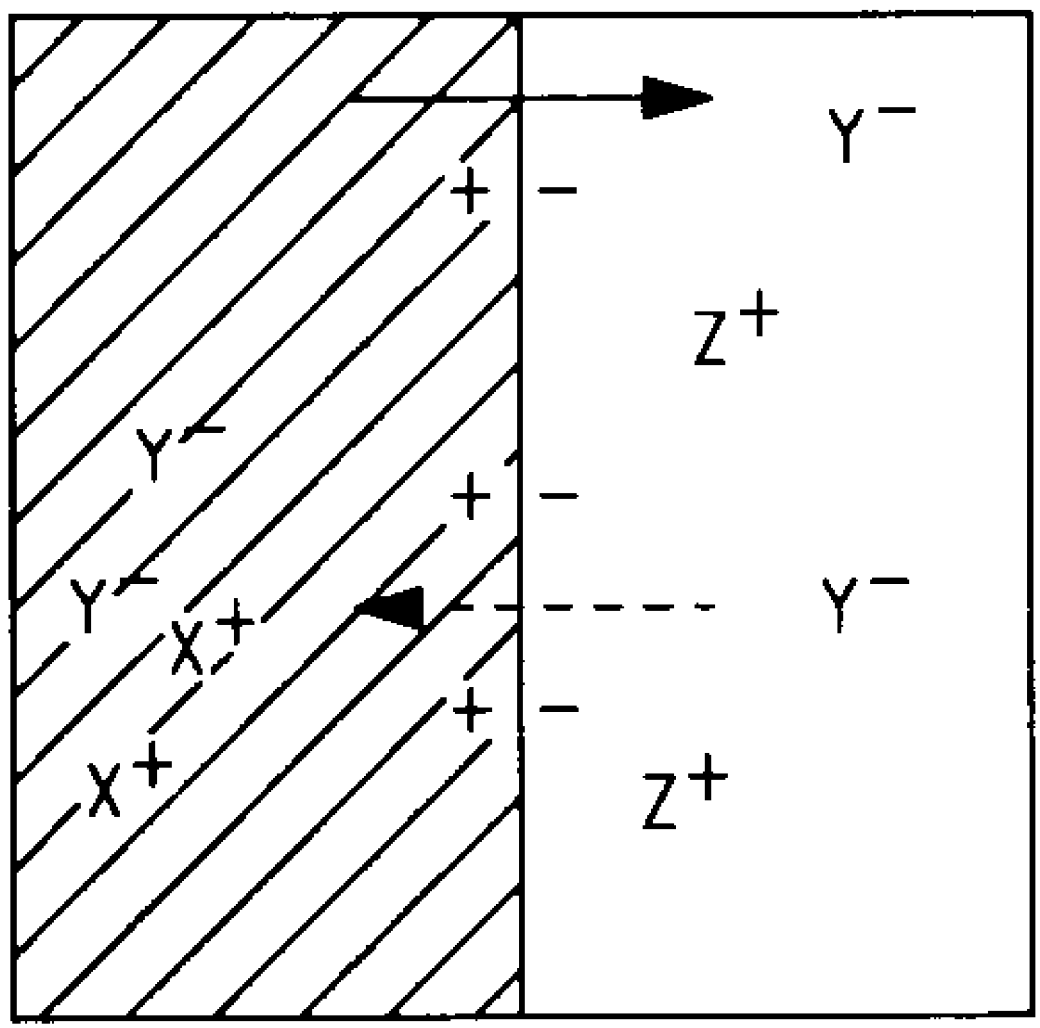
FIG. 4 illustrates the effects of establishing a LJP using two fluid streams that have equal total ion concentrations, but in which one ion (the cation in this case) is different in each stream and one ion is the same. The differing ions have different mobilities. In this case $Z^+$ has a higher mobility than $X^+$.

As will be apparent to one skilled in the art, the foregoing principles can be applied to establish LJPs to effect the desired transport of charged particles of varying size and charge within fluid streams in a microchannel. In addition, solution configurations other than the use of a single set of gradient-forming species at different concentrations in different fluid streams are possible to develop a LJP. For example, if all of the fluids have the same overall concentration of ionic species, but, different set of gradient-forming species that have one ion in common, a LJP will be generated as long as the differing ions have different mobilities. (FIG. 4).

It is also possible to generate a LJP with fluids that do not meet the above criteria if there is a net separation of charge developed when considering only the diffusive contribution to the net flux of ions This separation will occur whenever there is first, a concentration gradient for individual charged species and second, a difference between the average diffusivities of all the anionic species and the average diffusivities of all the cationic species. The averages must take into account the valence of the gradient-forming species as well. If the above criteria are met, then a separation of charge will develop and therefore a LJP will form.

This invention also provides for the use of multiple LJPs, either in series or in parallel in one or more microfluidic channels and devices. For example, a fluid containing extracted negative particles may be separated from other fluids in a channel via a microchannel outlet and may subsequently be used, for example, as the fluid containing negatively-charged particles in the reactor illustrated in FIG. 3H, or it may become the core fluid of the embodiment of FIG. 3F, wherein the particles are focused for analysis in flow cytometry. Such splitting of fluid streams using outlet channels and other means is well known and offers many combinations of methods in which LJP may be utilized.

The effects of the LJP on charged particle transport have been extensively modeled (see model details below), including the use of PE for focusing a protein, and for the selective fractionation of a protein from a fluid.

Passive electrophoresis can be utilized to improve flow cytometric methods. In a typical flow cytometer there is a core of fluid containing stained cells, which are counted as they pass through the focal waist of a laser. It is crucial that the cells pass one at a time through the laser and therefore, the more tightly focused the central stream, the more accurate the readings will be. Because most cells carry a charge, it is possible to use passive electrophoresis to further focus the cells to the midline of the channel. The focusing decreases the likelihood that multiple cells will pass the detector simultaneously.

This is accomplished using the 2-D sheath flow geometry described above (FIG. 3D). As discussed above, in this case the sheath fluid will have a negative charge relative to the core upon formation of a LJP. Here the central core is the analyte fluid containing the cells of interest and the two side streams are the sheath fluids. Since most blood cells have a negative charge at neutral pH, they are focused toward the center of the channel. If the particles to be focused are positively-charged, the relative ionic strengths of the fluids would be changed, such that the sheath fluid would have a positive charge relative to the core.

Figure 5:
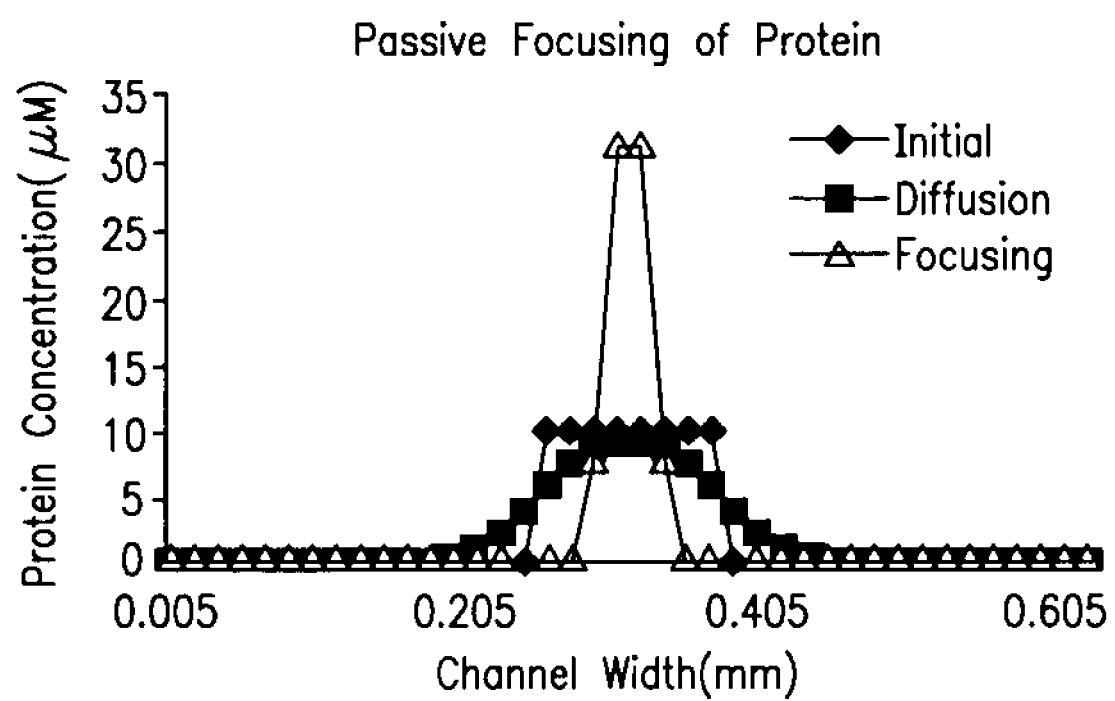
FIG. 5 illustrates the modeled focusing of protein in a microfluidic channel. The diamond curve represents the initial distribution of the protein across the microfluidic channel, the square curve represents the distribution due to diffusion only, and the triangle curve represents the effect on the distribution due to the LJP.

This two dimensional focusing has been modeled. In this simulation each of the two sheath streams are set to occupy 40% of the channel, with the central core occupying the remaining 20%. All the streams were buffered at the same strength at a pH of approximately nine. The sheath streams had a 500-fold greater electrolyte concentration than the core fluid. The model electrolyte used was sodium sulfate. In order to enhance the stability of the potential field, the diffusivity and mobility were reduced. This serves as an accurate model of an anionic polymer. The modeled concentration profiles for proteins located in the center stream of the channel are shown in FIG. 5. In FIG. 5, the diamond curve represents the initial distribution of the protein across the microfluidic channel, the square curve represents the distribution due to diffusion only, and the triangle curve represents the effect on the distribution due to the LJP. This figure shows a clear focusing of the protein into a tighter band in the center of the channel. Here a protein is used in the model, but the model applies equally to any negatively-charged particle.

Figure 6:
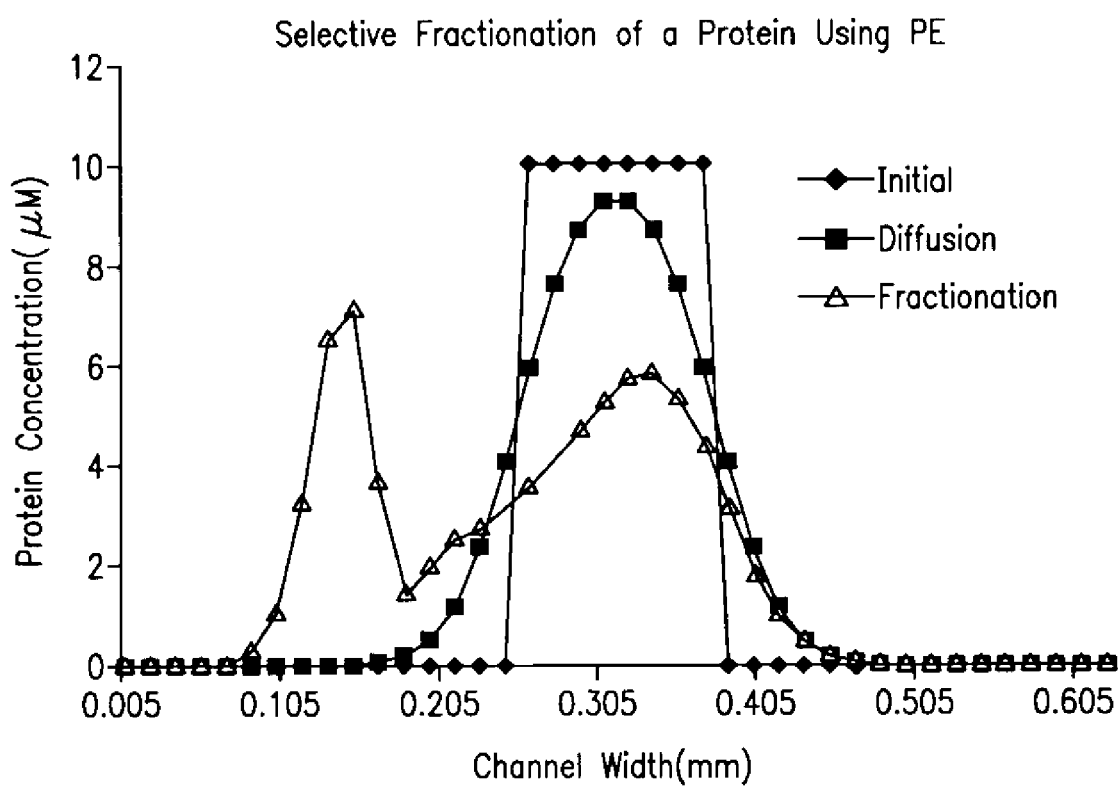
FIG. 6 illustrates the modeled selective fractionation of a charged particle of interest, i.e., a protein, in a microfluidic channel in which a core fluid containing the protein is flanked on two sides by sheath fluids forming oppositely-charged LJPs at each interface. The diamond curve represents the initial concentration of protein across the channel width. The square curve represents the diffusion of the protein in both directions in the absence of the LJP. The triangle curve represents the fractionation of the protein (selective transport) across the LJP formed between the left sheath fluid and the core fluid.

In the 2-D flow geometry, it is not necessary to use identical sheath fluids on both sides of the core. By using asymmetric sheath fluids, fractional separation of charged species is achieved. Consider the flow geometry of three parallel flow streams. If a potential is induced across one interface but not the other, a protein located in the core fluid is moved only relative to that interface. A simulation was done that demonstrated this phenomenon. The relative flow rates were assigned in the same way as the focusing example. Sodium sulfate was again used as the model electrolyte. In this case, it was necessary to slow the diffusivity and mobility of the sodium. This situation accurately models a cationic polymer. The core fluid and the left hand sheath stream had identical ionic strengths that were higher than the right-hand sheath fluid. The core fluid also contained protein as the species of interest. In this case, the negative ion moves faster then the positive. As the ions diffuse out of the core fluid into the right-hand sheath fluid, the core fluid becomes positive relative to the right-hand sheath fluid. This causes the negatively-charged protein to move away from the right interface. The result is an overall shift to the left of the negatively-charged species. This model behavior can be seen in FIG. 6. In FIG. 6, diamonds represent the initial concentration of protein across the channel width. Squares represent the diffusion of the protein in both directions in the absence of the LJP. Triangles represent the fractionation of the protein (selective transport) across the LJP formed between the left sheath fluid and the core fluid.

In the case of slowly-diffusing particles that have a positive charge, the positively-charged particles will move towards the right-hand sheath fluid while the negatively-charged particles still move towards the left hand side. In this way fractional separation of differently charged species could be accomplished using passive electrophoresis.

Figure 7:
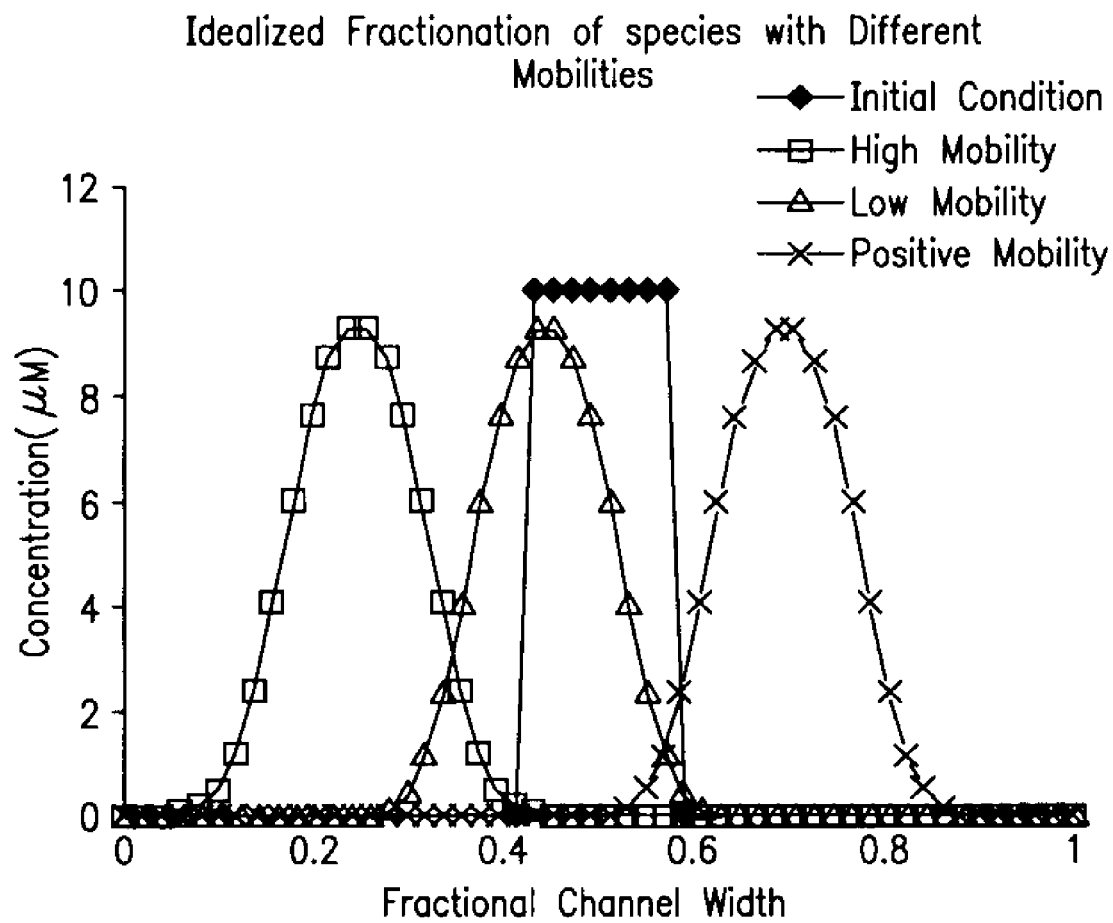
FIG. 7 illustrates modeled fractionation of charged particles of interest (proteins) of different charge and mobility in a microchannel in which a core fluid containing the protein is flanked on two sides by a sheath fluids forming oppositely-charged LJPs at each interface. The diamond curve represents the initial condition of the system where all the protein particles are contained in the core fluid. The square cure shows how protein particles of high mobility and negative charge move into the left fluid. The diamond curve shows how protein particles of low mobility and negative charge moves less far into the left fluid. The X Curve shows how protein particles having a positive charge move into the right fluid. The squares and triangles represent negatively-charged proteins with different electrophoretic mobilities. The X curve represents a protein whose net charge is positive.

Separation of charged particles is not limited to particles of opposite sign. Any two populations of particles of varying electrophoretic mobility can be separated. The electrophoretic mobility is a function of the net charge and the friction factor for the particles in solution. On this basis it is possible to separate two particles that are of different sizes, such as two proteins of different sizes. Two particles that are of different shapes, for example a globular protein and a filamentous protein, can also be separated. It is also possible to separate two particles that have different net charges, such as two proteins with similar shape and size but one being more negative than the other. Passive electrophoresis can be used to separate two particles with any combination of these factors that lead to a net difference in electrophoretic mobility. A graphical representation of how this type of fractionation might occur is shown in FIG. 7. In this case, three fluids are injected into the channel. As in the example above, the core fluid and the left hand sheath stream have identical ionic strengths that are higher than the right-hand sheath fluid. The core fluid also contains several charged proteins. In this case, the negative ion moves faster then the positive. As the ions diffuse out of the core fluid into the right-hand sheath fluid, the core fluid becomes positive relative to the right-hand sheath fluid. In this case there are three different proteins located in the initial core fluid. The squares and triangles represent negatively-charged proteins with different electrophoretic mobilities. The X curve represents a protein whose net charge is positive and thus moves in the opposite direction (right). FIG. 7 shows the migration of each protein relative to the initial condition at some length down stream.

Modeling the Liquid Junction Potential

LJP may be measured using appropriate electrode systems designed to measure potential differences between the two sides of the fluid interface. To do so, electrodes are placed on either side of the microchannel, perpendicular to the plane of the fluid interface. Such a system comprises, for example, silver/silver-chloride electrodes in the sidewalls of the channel, when measuring a junction potential in which chloride ions are involved. Because the LJP varies predictably down the length of the channel, the ideal measurement electrodes span a very small length of channel. The silver chloride coating on the electrodes acts as a thermodynamic reference allowing for the stable measurement of the liquid junction. The potential difference between the electrodes can either be measured directly or amplified prior to measurement.

Alternatively, the distribution of mass (charged particles) is modeled as a function of the LJP. The following model includes the dominant phenomena necessary to determine if deviations from the standard diffusion profiles observed in the presence of a conductivity gradient are in fact a result of an LJP and not some other phenomenon. A complete discussion of the applicability of the model can be found in this section. A similar model describes the dominant electrokinetic, diffusive and convective phenomena in microchannels (Cabrera, C. R., et al., Anal Chem 2001, 73, 658–666) and the present model is disclosed in Munson, et al. (Munson, M. S. et al., Electrophoresis 2002, 23, 2642–2652), incorporated in its entirety herein by reference to the extent not inconsistent herewith.

Figure 2B:
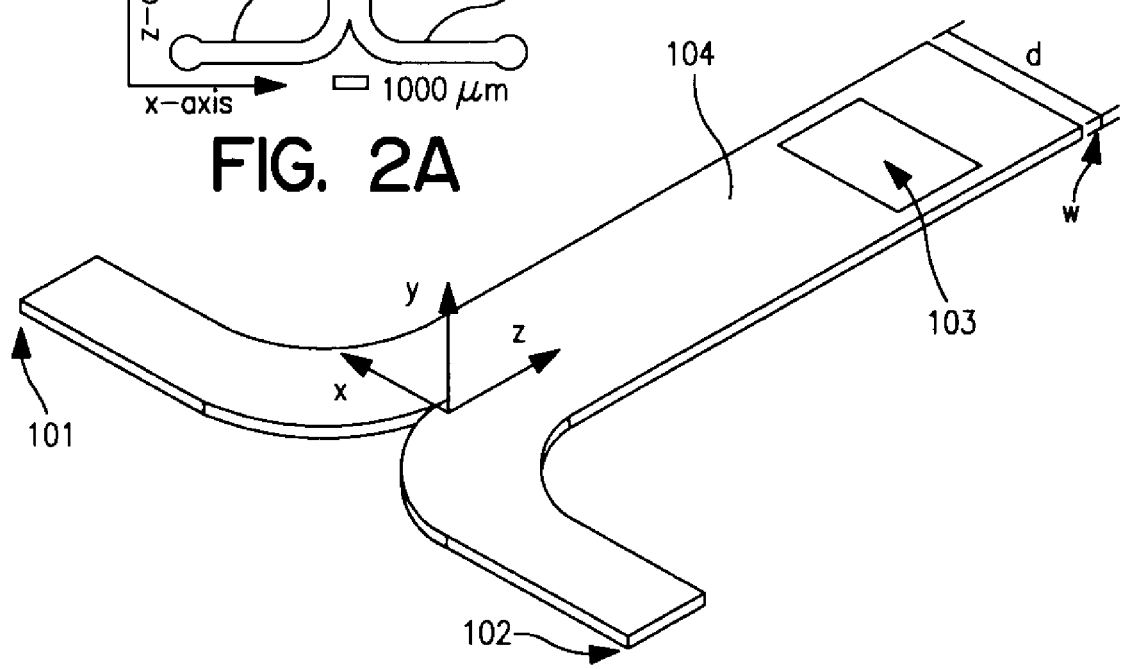

Using Matlab (The Mathworks, Natick, Mass. USA), a custom-coded a two-dimensional finite difference model of the electrochemical, mass transport, and acid/base equilibrium phenomena occurring in a microfluidic electrochemical flow cell has been developed. Model development (Munson, M. S. et al., Electrophoresis 2002, 23, 2642–2652) was based on a previously described formulation (Lindgren, E. R., et al., in: Tedder, et al., Eds, Emerging Technologies in Hazardous Waste Management V, American Chemical Society: Washington, D.C., 1995, pp 48–62) and is similar to models that have been developed by other groups (Vazquez, M., et al., D., Anal Chem, ASAP Article 2002, Apr. 4, 2002; Mosher, R. A., The dynamics of electrophoresis/R. A. Mosher, D. A. Saville, W. Thormann; VCH, Weinheim; New York:, 1992; Bier, M., Palusinski, et al., Science 1983, 219, 1281–1287). The physical phenomena considered are electrophoretic migration and diffusion in the x-direction and convective transport in the z-direction. The system is assumed to be at steady state. The model solves for the steady-state solution to the equation of continuity, tracking changes in both the x-direction and z-direction (FIG. 2B). The system is assumed to be uniform along the y-direction. The full continuity equation, written in terms of mass conservation, (Equation 1) is shown below $$\frac{\partial}{\partial t} c_i = -(\nabla \cdot \{c_i \vec{v} + \vec{J}_i\}) + r_i. \tag{1}$$

Here $c_i$ is the concentration of species 'i', is the fluid velocity, $J_i$ is the mass flux due to electromigration and molecular diffusion, of species 'i', and $r_i$ is the net rate of reaction of species 'i'. A detailed example of one application of the model is described here. The following species were considered in this model; $H^+$, $OH^-$, fluorescein, fluorescein$^-$, fluorescein$^{-2}$, AMPSO$^-$, AMPSO, AMPSO$^+$, Na$^+$, and the gradient-forming species (Na$^+$ and Cl$^-$ or Na$^+$ and SO$_4^{-2}$). The following three equilibrium reactions were considered:

$$H^+ + OH^- \underset{K_w}{\longleftrightarrow} H_2O, \tag{2}$$

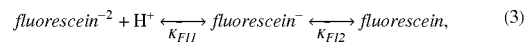

$$fluorescein^{-2} + H^+ \underset{K_{F11}}{\longleftrightarrow} fluorescein^- \underset{K_{F12}}{\longleftrightarrow} fluorescein, \tag{3}$$

and

$$AMPSO^+ \underset{K_{A1}}{\longleftrightarrow} AMPSO \underset{K_{A2}}{\longleftrightarrow} AMPSO^-, \tag{4}$$

where $K_W$ is the equilibrium constant for water, $K_{F11}$ and $K_{F12}$ are the equilibrium constants for fluorescein and $K_{A1}$ and $K_{A2}$ are the equilibrium constants for AMPSO.

Equation 1 was simplified based on the following assumptions:

Transport along the axial (z-direction) due to diffusion and electrophoresis was neglected ($J_z=0$) because the effects of convective mass transport were assumed to be significantly larger. At the flow rate for which the model and experimental results were compared, the characteristic length scale for the diffusion of protons, the most rapidly-diffusing species in the system, is 61

μm (using a diffusion coefficient of $9.3 \times 10^{-5}$ cm$^2$/s (Lide, D. R., CRC Handbook of Chemistry and Physics, 75th ed.; CRC Press, Cleveland, Ohio:, 1995)). The characteristic length scale for convection is 4000 μm. The difference in the scales over which these effects occurs allows us to neglect axial diffusion.

Entry and exit effects on fluid flow and mass transport are neglected; that is, the flow is assumed to be fully developed immediately upon entering the channel. The typical entry lengths have been measured for similar devices (Kamholz, A. E., et al., Biophys J 2001, 80, 1967–1972) to be on the order of 100's of microns. Since flow is laminar, this assumption implies that the fluid velocities in the x and y-direction are zero.

The system is assumed to be homogenous along the y-direction ($J_y$=0). A detailed discussion of the validity of this assumption follows below.

In this example, the only chemical reactions anticipated to occur in the channel are acid/base equilibrium reactions. Because the typical rates of reaction for acid/base equilibria are rapid in comparison to the rates of mass transport, these reactions can be accounted for in a separate module within the model. This allows for the numerical decoupling of the transport and reaction terms in the governing equation.

The diffusive flux here was assumed to be Fickian in nature. Research by Skryll (Skryll, Yu., PCCP Phys Chem Chem Phys 2000, 2, 2969–2976) has shown that for the early stages of junction formation, this is not accurate and a hyperbolic model of diffusion ($\partial C/\partial t = -D_i^* \partial^4 C/\partial x^4$) should be used. However, the time scales investigated in this research (approximately seconds) are much longer than those investigated in Skryll. These two descriptions are comparable at longer time scales, so the assumption of Fickian diffusion is appropriate.

After accounting for the assumptions described above and solving for the steady-state solution, Equation 1 was simplified as follows $$\frac{\partial c}{\partial z}i = -\frac{1}{v_z}\nabla \cdot \vec{J}_i \qquad (5)$$

where the flux J is described by $$J_{i,x} = -\mu_i^e \frac{\partial \Phi}{\partial x} - D_i \frac{\partial c}{\partial x} i \qquad (6)$$

Here, μ is the electrophoretic mobility of species 'i', Φ is the electrostatic potential, and D is the diffusivity of the species. Equations 5 and 6 are the governing equations of the mass transport phenomena only. The chemical reactions are accounted for using the algebraic equilibrium expression suggested by Equations 2–4. This description of the mass flux in the channel assumes that the solutions are ideal (unity activity coefficients). The experimental conditions employed here violate this assumption, but, we believe that for the purposes detailed here, which are to confirm that junction potentials affect the distribution of mass in a microchannel in a manner consistent with the experimentally observed data, the violation of this modeling assumption is permissible.

The field term ($\partial \Phi/\partial x$) was defined by substituting the equation for flux into a statement of charge conservation leading to Equation 7

$$\frac{\partial \Phi}{\partial x} = -\frac{1}{F^2 \sum z_i^2 \mu_i C_i}\left(F \sum z_i D_i \frac{\partial C_i}{\partial x}\right) \qquad (7)$$

where F is Faraday's constant, $z_i$ is the valence of species 'i', and the summations are computed over all the charged species in the solution. A detailed discussion of this derivation is presented elsewhere (Lindgren, E. R., et al., in: Tedder, et al., Eds, Emerging Technologies in Hazardous Waste Management V, American Chemical Society: Washington, D.C., 1995, pp 48–62). The potential drop across the channel (Φ) was calculated by numerical integration of the field data. Note that the Poisson equation was not explicitly solved. A statement of charge conservation was used instead. To test the validity of this choice, a separate model was developed that calculated the field by solving the Poisson equation. For the simplified case where only Na$^+$, Cl$^-$, H$^+$ and OH$^-$ were considered, the results of this model were identical to those of the model presented here for residence times longer than 0.1 ms (data not shown).

The y-direction is assumed to be homogenous throughout the model. For the narrow 'w' (width in the y-direction) of the device under investigation, this is a valid assumption at the position down the channel at which our observations where made. Previous research has confirmed, through both model (Kamholz, A. E., et al., Biophys J 2001, 80,155–160) and experiment (Kamholz, A. E., et al., Biophys J 2001, 80,1967–1972) for a two-inlet T-Sensor experiment in the same channel geometry used here, that the non-uniform velocity profile in the y-direction will result in a transient concentration gradient along that dimension. However, the diffusive flux along the y-direction will homogenize these gradients at the position at which our experimental data was taken. As part of this previous research, it was found that for slowly-diffusing macromolecules such as proteins, at very low flow rates the effect of the non-uniform velocity profile on concentration profiles is more significant, while for small molecules, such as fluorescein, this exaggerated effect was observed only at the slowest flow rates (~10 nL/s) (Kamholz, A. E., et al., Anal Chem 1999, 71, 5340–5347). However, the flow rate (125 nL/s) that corresponds to the experimental data selected for comparison to model results is sufficiently high that the concentration profile along y-direction can be assumed to be homogenous at the observation position down the channel.

Velocity profile-dependent dispersion of solute in the axial direction is described by Taylor dispersion when concentration profiles in the y-direction are approximately uniform. For Taylor dispersion, the typical standard that is applied to determine if the Taylor regime has been reached is described by the inequality, $$\frac{L}{\bar{v}} \gg \frac{w^2}{D_i}, \qquad (8)$$

where L and w are geometrical parameters described in FIG. 2, $\bar{v}$ is the average linear velocity and $D_i$ is the diffusion coefficient of the species of interest. When this inequality is satisfied, a typical diffusing species will have had adequate time to "sample all accessible transverse streamlines many times before axially exiting the system" (Dorfman, K. D., et al., J Appl Phys 2001, 90, 6553–6554). This inequality does hold for the lower flow rates studied here, which are the experimental data to which the model is compared. However, because the concentrations are uniform along the y-direction at the inlet, uniformity is reached at length scales shorter than those implied by Taylor dispersion theory. Further discussion of this assumption can be found (Kamholz, A. E., et al., Biophys J 2001, 80, 155–160; Kamholz, A. E., et al., Biophys J 2001, 80,1967–1972; Dorfman, K. D., et al., J Appl Phys 2001, 90, 6553–6554; Beard, D. A., J Appl Phys 2001, 89, 4667–4669; and Beard, D. A., J Appl Phys 2001, 90, 6555–6556).

A two-step approach was used, similar in concept to the Euler-LaGrange method, for solving problems with stiff moving boundaries. First, species undergo mass transport for a fixed length step down the channel, modeled by solving a system of finite-difference equations based on Equation 1. Second, the resulting concentrations of weak acids and bases are recalculated at each node to comply with their corresponding $pK_a$'s, while conserving mass and charge. The predictions of this model have been verified with experimental data for the case of an applied voltage (Cabrera, C. R., et al., Anal Chem 2001, 73, 658–666). Extension of the model to cover this problem is achieved by setting the applied voltage to zero. Applying this model to LJP formation in microfluidic devices is appropriate because it includes the dominant phenomena in the channel during LJP formation.

This model may be used not only to verify that experimental observations are the result of the presence of a LJP, but may also be used as a predictive tool for the design of microfluidic systems and parameters, including the choice of gradient-forming species.

One skilled in the art can use the foregoing model to design systems for controlling the movement of charged particles such as cells with respect to an interface between adjacent streams. The parameters necessary for doing so include the mobility, concentration, valence and pH dependence of all charged species in the channel, as well as the rates of any reactions, if they occur. For example the distance the charged particles (of known or calculable electrophoretic mobility) are required to move can be used to determine the potential required across the fluid interface in accordance with the foregoing model. Ions are selected for use in the adjacent streams, and their mobilities as well as the required potential across the fluid interface are used to calculate the required concentration of ions to use. As will be appreciated by those skilled in the art, when the magnitude of an LJP and/or ion concentrations are pre-determined, the system can be designed, using the foregoing model, with channel geometries which will produce the required separations, mixing, focusing, etc., based on the distance the charged particles will travel under these known conditions of LJP and/or ion concentration.

EXAMPLES

The following examples illustrate the utility of the LJP in microfluidic devices, and are not meant to be limiting. Experimental results are compared to those predicted by the model discussed above.

The flow cell used in the following examples comprised an H-filter (Weigl, 1999), which is an H-shaped channel etched in silicon and sealed with borosilicate glass (see FIG. 2A), although the experiments could have been performed in any optically interrogable microfluidic channel. It is important to note that the use of LJPs, as taught herein, are useful with any microfluidic channel in which two or more fluids are in laminar flow with each other. The device was fabricated using the facilities of the Washington Technology Center. A complete description of the fabrication process can be found elsewhere (Kamholz, 1999). The channel has a width (distance along the optical axis), w, of 10 μm and a diffusion dimension, d, of 1.4 mm (See FIG. 2B). The main portion of the channel had a length L of 7 mm. The flow cell was mounted in a manifold that provided fluidic interconnections between the microchannel and the pumping system, as well as facilitated mounting the channel on the microscope stage. As illustrated, two fluids flow in parallel laminar flow within the H-filter such that diffusion occurs in the d direction. The distribution of a fluorescent tracer in the channel was monitored 4 mm from the inlet point (See FIG. 2) using an inverted fluorescence microscope (IM-35, Carl Zeiss, Thornwood, N.Y., USA) with a mercury arc light source. Two fluids were injected into the microchannel using positive displacement syringe pumps (Kloehn Co, Ltd., Las Vegas, Nev., USA). The two outlets were left open to the atmosphere. The solution pairings for each of the following three experiments are shown in Table I:

TABLE 1

| Experimental Solution Pairings | | |
|---|---|---|
| | Left Side of Channel | Right Side of Channel |
| Control Example 1 | 9 μM Fluorescein<br>0.13 mM AMPSO | 0.13 mM AMPSO |
| Example 2 | 9 μM Fluorescein<br>0.13 mM AMPSO | 1 M NaCl<br>0.13 mM AMPSO |
| Example 3 | 9 μM Fluorescein<br>0.13 mM AMPSO | 1 M $Na_2SO_4$<br>0.13 mM AMPSO |

Reagents

All reagents were used as received without additional purification. All solutions were made in a 0.13 mM 3-([1,1-dimethyl-2-hydroxyethyl]amino)-2-hydroxypropane-sulfonic acid (AMPSO) (Sigma, St. Louis, Mo., USA) buffer. The compositions of the solutions used in these experiments are summarized in Table 1. The solutions contained combinations of fluorescein (excitation 494/emission 520) (Sigma, St. Louis, Mo., USA), NaCl (J. T. Baker, Phillipsburg, N.J., USA), and $Na_2SO_4$ (J. T. Baker Phillipsburg, N.J., USA). All solutions were made in deionized (DI) water. The measured pH of these solutions ranged from 9.3 to 9.5. The fluorescence emission of all fluorescein-containing solutions were compared in a cuvette using a fluorimeter (L5-50, Perkin Elmer, Wellesley, Mass., USA); there was no measurable difference in emission intensity due to the variations in ionic composition or the pH ranges used in these experiments.

Experimental Protocol

Prior to all experiments, all sample lines and devices were washed with 10% v/v bleach (5.25% sodium hypochlorite: SYSCO Corp., Houston Tex.) solution. The purpose of this was to reduce the background fluorescence in the channel due to adsorbed materials from other experiments. Following the wash, the system was rinsed with DI water. To ensure complete rinsing, a volume no less than time times the volume of the channel and associated tubing was pumped through the device. Both solutions were injected at equal flow rates. The flow rates of the two solutions were varied in order to vary the average residence time at a given distance downstream. The flow rates ranged from 21 nL/sec to 1.3 µL/sec, corresponding to average residence times ranging from 2.7 sec to 0.042 sec, and average linear velocities of 0.15 cm/sec to 9.5 cm/sec. After each combination of solutions was tested, images of the channel with only labeled solution ("flood" image) and only the unlabeled solution ("background" image) were collected at the highest and lowest flow rates.

Image Processing

Figure 8B:
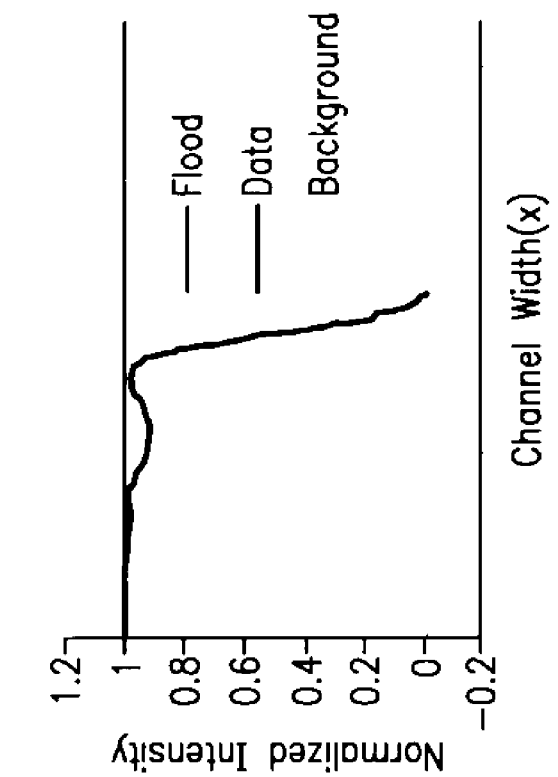
FIG. 8 illustrates the transformation of raw data to a corrected and normalized concentration profile for a representative data set. The data collected represent the distribution of fluorescent intensity in a microfluidic channel when two fluids are brought into contact and flow in adjacent laminar flow. Two additional profiles are required to fully normalize a data set. The required profiles represent the intensity profile of the channel filled only with the label containing solution, the so called 'flood' profile, and of the channel filled only with the solution not containing the label, the so called 'background' profile. Point-by-point, the background profile is subtracted from each data profile and from the flood profile, these modified profiles are referred to as 'background-corrected'. The background-corrected data images are then divided (point by point) by the background-corrected flood image. This process is referred to as normalization.
Figure 8A:
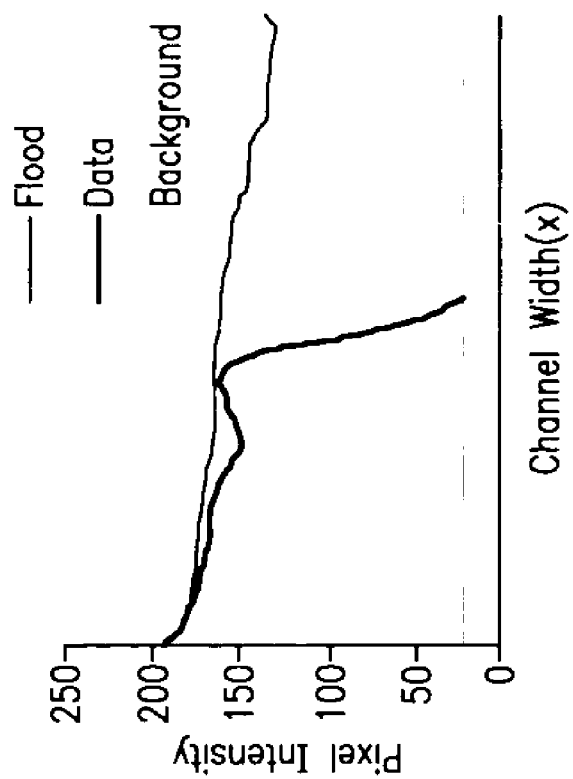

Fluorescence images were collected 4 mm from the point where the fluids first come into contact. A 3-chip chilled color CCD camera (Oncor, Gaithersburg, Md., USA) was used to image the channel. The output from the camera was collected using a PC based frame grabber (CG-7, Scion Co., Frederick, Md., USA). The focal plane of the microscope objective was adjusted to be approximately at the midplane of the channel. All images were taken using a 10×objective, corresponding to a pixel size of 2.3 µm square. The depth of field of this objective is reported by the manufacturer to be 8.5 µm. This is sufficient to ensure line-of-sight integration through the 10 µm depth of the channel, provided that the focal plane was positioned sufficiently close to the midplane of the device. An exposure time of 0.17 sec was used. Three replicate images were captured at each flow rate. All images were read into Matlab where the green channel data were converted into a matrix of intensity values. The camera response is linear with image intensity; therefore the intensity of each pixel value is directly proportional to the fluorescein concentration at that location at a fixed pH (Kamholz, A. E., et al., Biophys J 2001, 80, 155–160). Ten adjacent rows of pixels along the flow direction were averaged to give a single intensity profile across the width of the channel. This window represents a differential in average residence time of 0.23 ms at the highest flow rate and 14 ms at the lowest flow rate. These time frames are on smaller time scale than the phenomena considered here, and thus this averaging is justified in order to enhance the signal to noise ratio. The intensity profiles for each of the three replicate images were then averaged. Flat-field and background correction were employed to correct for the non-uniformity of the excitation light and collection efficiency, and to normalize the intensity profiles. The background profile was subtracted from each intensity profile. The background-corrected intensity profiles were then divided by the background-corrected profile of the flood image. The transformation from raw data to a corrected and normalized concentration profile is shown for a representative data set in FIG. 8.

Calculating the Rate of Mass Transport

The relative rates of mass transport across the mid-plane of the channel were calculated by numerically integrating the intensity profile. The integral of half the intensity profiles was compared to the integral of the entire intensity profile in order to calculate the percentage of the total fluorescent tracer that crossed the mid-plane. These values were calculated for each of the three replicate images, and the standard deviation was taken as a measure of the error. The fractions crossing the midline in the two cases where junction potentials were generated were normalized by dividing these values by the fraction of mass crossing the midline when no junction potential was formed.

These experiments represent control experiments and two functions of the junction potential: acceleration and deceleration of the mass transport of an ionic species.

Control Example 1

Free Diffusion

Figure 9:
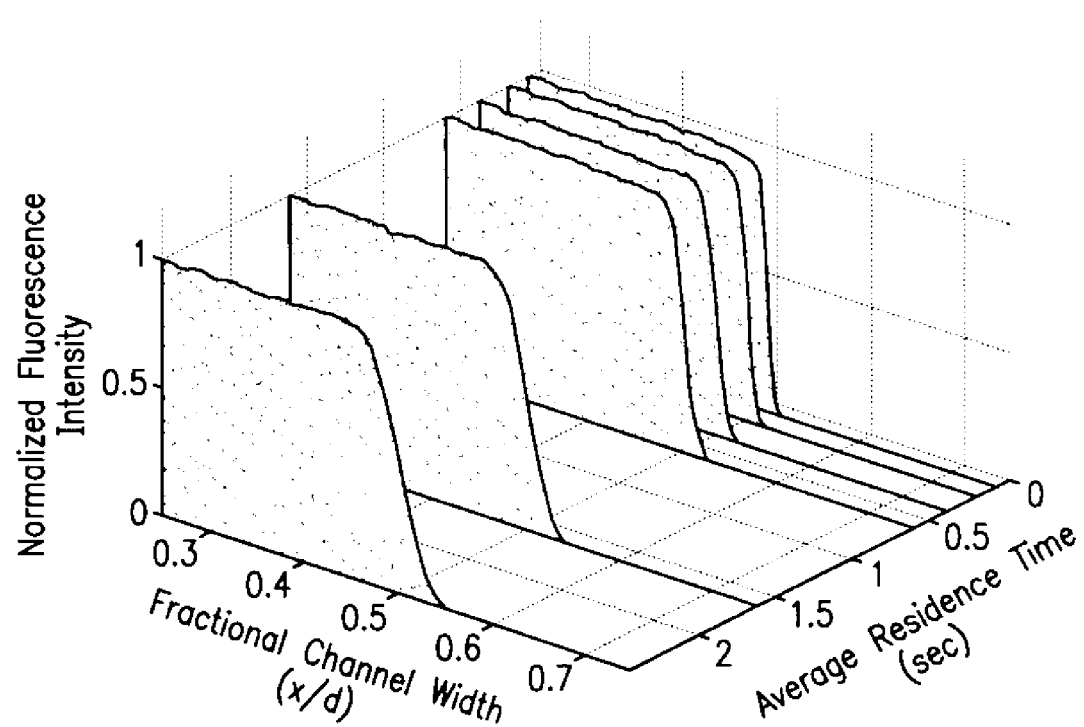
FIG. 9 illustrates results from control experiment 1. The solution contents are described in Table 1. No junction potential is anticipated. The normalized fluorescence intensity profiles are shown for average residence times of 0.075, 0.2, 0.4, 0.6, 1.6, and 2.7 seconds. The system behaves in a manner consistent with what is expected from free diffusion.

Experiment 1 (conditions shown in Table 1) served as a control for the rest of the experiments; it represents the case where no LJP was formed because the ionic compositions of the fluid pairs were balanced. In this case it was expected and observed that diffusion was the only mechanism of transverse mass transport. The results from the diffusion experiment are shown in FIG. 9. Addition of either 1 M NaCl or 1 M $Na_2SO_4$ to both streams produced results that were indistinguishable from the control.

As the residence time increased, the extent of interdiffusion increased, as expected; slope of the concentration profile at the midline of the channel are less steep. It is interesting to note that at the midline, the concentration rapidly reached the equilibrium concentration, and then remained fixed. Thus, the concentration profiles appeared to 'pivot' about this point with increasing residence time. These results are in good agreement with other experiments that monitor the transverse diffusion of a freely-diffusing species in an H-filter (Kamholz, 1999; Kamholz, A. E., et al., Biophys J 2001, 80,155–160; Kamholz, A. E., et al., Biophys J 2001, 80, 1967–1972), and indicate that diffusion is the only significant mechanism for transverse mass transport in this system.

Example 2

Accelerating Mass Transport Using LJP

Figure 10:
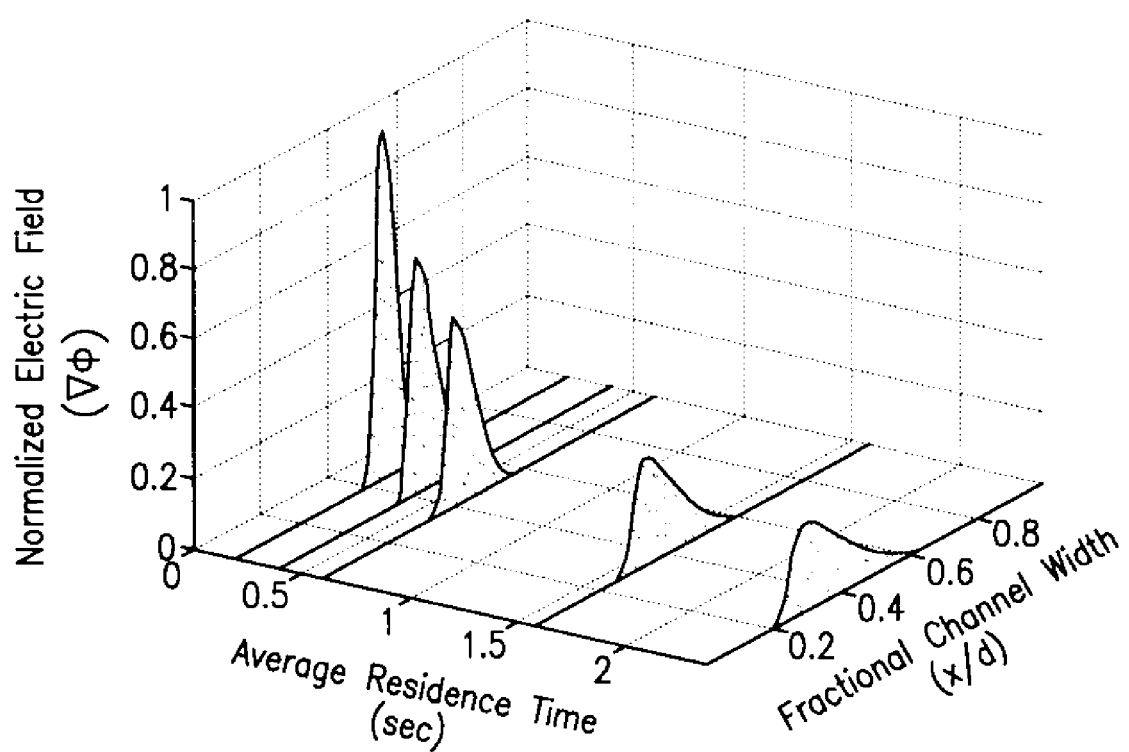
FIG. 10 illustrates the predicted field as the result of the LJP formed in Experiment 2. The field values were normalized to the maximum amplitude (0.072 V/cm) of the field at the earliest time point (0.2 Sec). The field was not computed at the 0.075 Sec time point. The potential can be calculated by integrating the field curve with respect to channel width (x/d).
Figure 11:
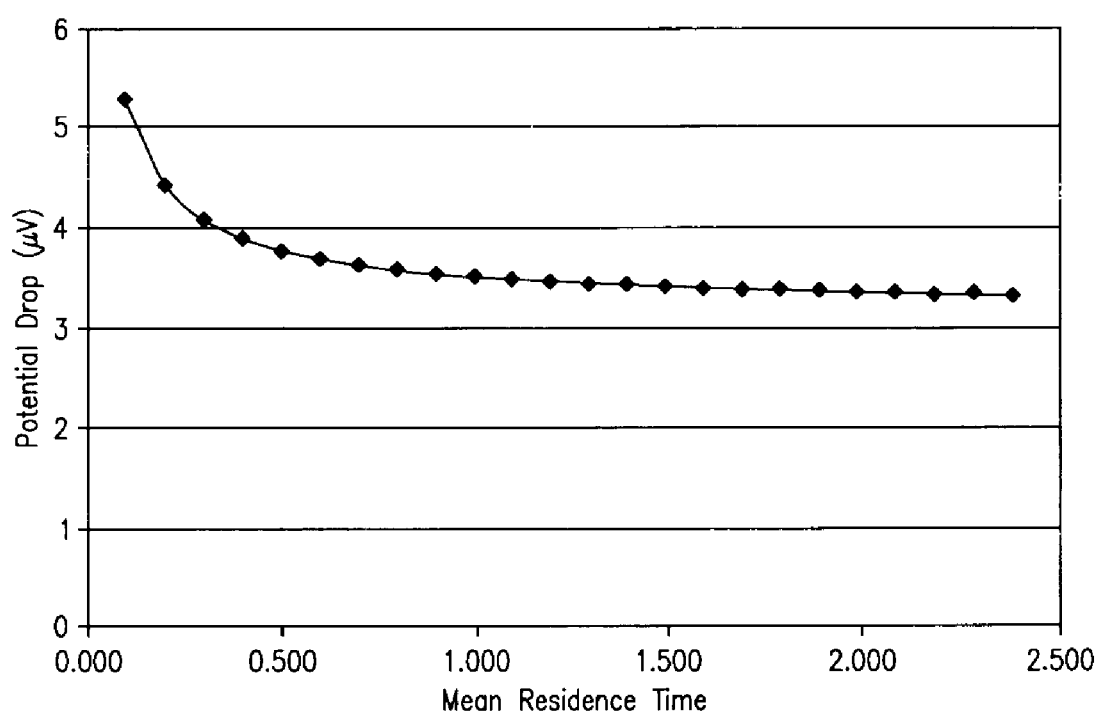
FIG. 11 illustrates the potential as a function of residence time, as predicted by the model. The potential drop across the channel was calculated by numerical integration of the field profiles.
Figure 12:
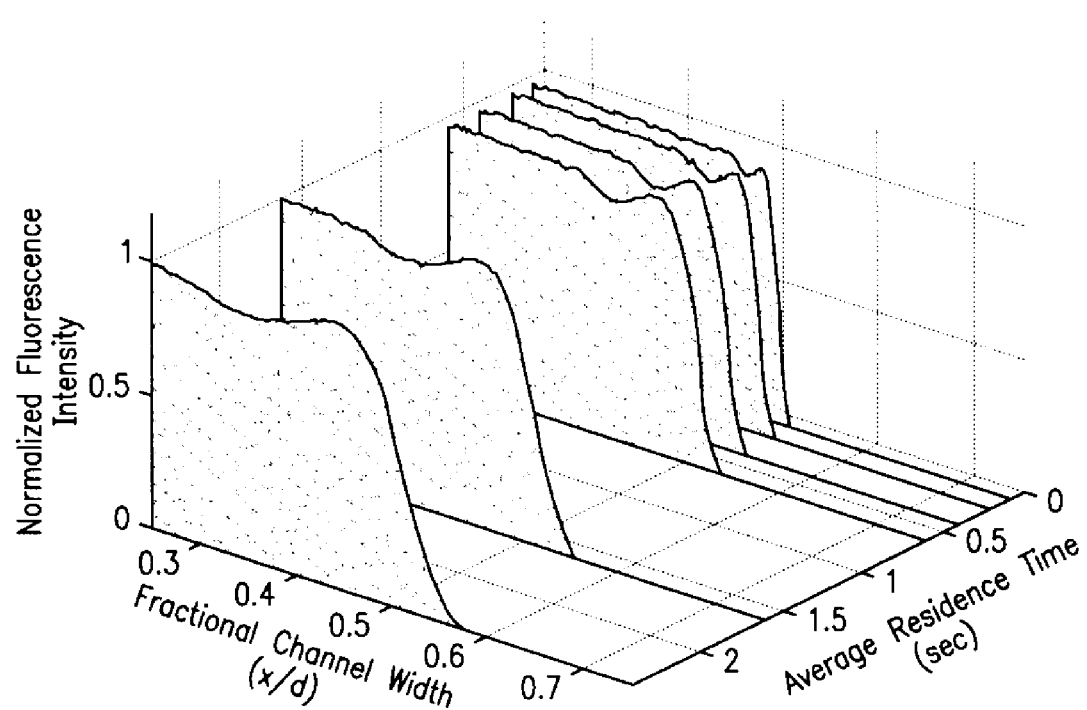
FIG. 12 illustrates the experimental results from Experiment 2 (particle acceleration using a LJP). The microfluidic channel contents are described in Table 1. The normalized fluorescence intensity profiles are shown for average residence times of 0.075, 0.2, 0.4, 0.6, 1.6, and 2.7 seconds. The behavior of this system shows significant departures from the prediction for a freely-diffusing species, indicating that the LJP has a measurable effect on the distribution of the charged tracer fluorescein in the channel.
Figure 13:
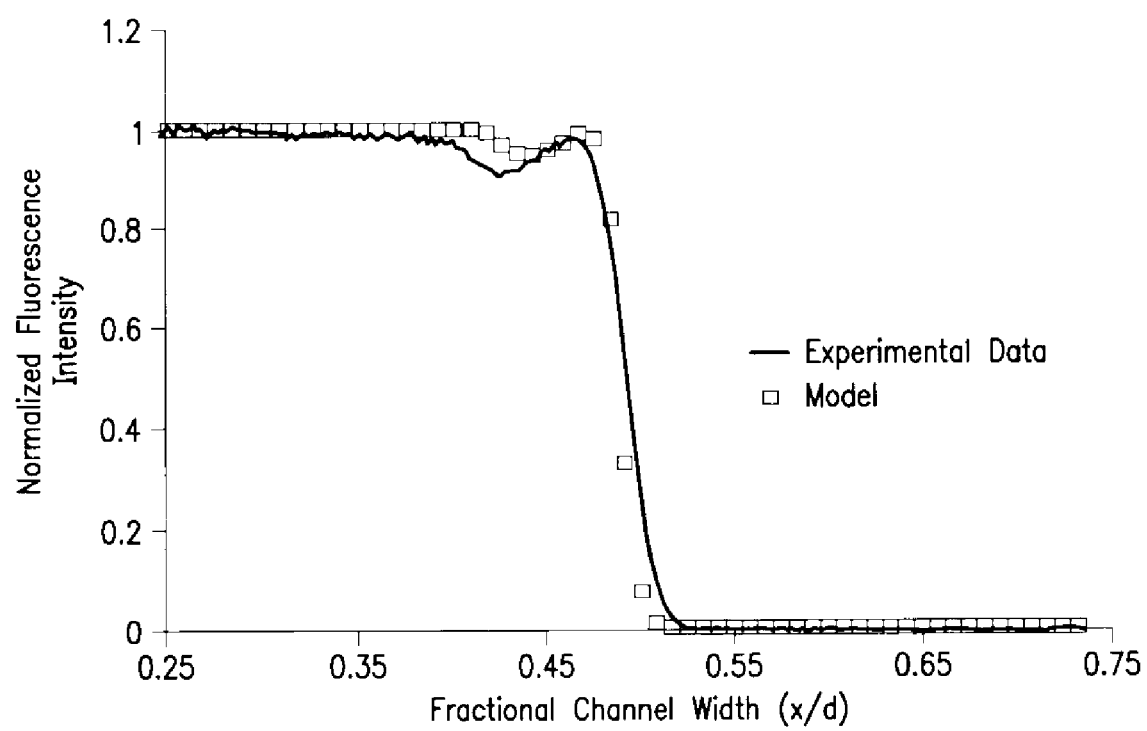
FIG. 13 illustrates a comparison of experimental data (—) from Experiment 2 to the model (□). The results from the mathematical model are compared to the experimental results at an average residence time of 0.4 sec. Qualitative agreement is seen in that the model predicts the major features of the experimental data.

In Experiment 2, the unlabeled solution contained a high concentration of NaCl and the labeled solution contained no NaCl. It was expected that this would generate a LJP because the diffusivity of $Na^+$ ($1.33 \times 10^{-5}$ $cm^2$/sec) is 45% slower than that of $Cl^-$ ($2.03 \times 10^{-5}$ $cm^2$/sec) (Lide, D. R., CRC Handbook of Chemistry and Physics, 75th ed.; CRC Press, Cleveland, Ohio, 1995). Based on the model prediction of the field (FIG. 10) and potential (FIG. 11), we expected that negatively-charged fluorescein would experience an electrophoretic force acting in the same direction as the diffusive transport, thereby accelerating its net flux across the midline. The resulting concentration profiles from this experiment are shown in FIG. 12, which show a depletion of the fluorescein in a region of the labeled solution near the interface; there was a 'dip' in the normalized intensity profile. This dip is caused by the electrophoretic migration of dye near the interface across the midline. The decrease in fluorescence intensity, and therefore fluorescein concentration, was matched by a corresponding increase in the amount of dye on the other half of the channel. This dip is predicted by the mathematical model, as seen in FIG. 13.

The nature of the depletion zone is a function of the residence time. In FIG. 11, we see that the depletion was formed almost immediately after the fluids were brought into contact, and took on its largest magnitude at this time, as measured as the depth of the dip. This is consistent with the prediction that during the early stages of potential formation, the field strength would be highly localized at the center of the channel and take on its highest values. As the gradient of the potential-forming species (in this case NaCl) became less steep, the depletion zone became broader and shallower. The region broadened because the field began to occupy larger fractions of the channel. The region became shallower because as the field strength declined and the electrophoretic velocity of the fluorescein decreased, fluorescein was able to diffuse back into the depletion region.

Example 3

Decelerating Mass Transport Using LJP

Figure 14:
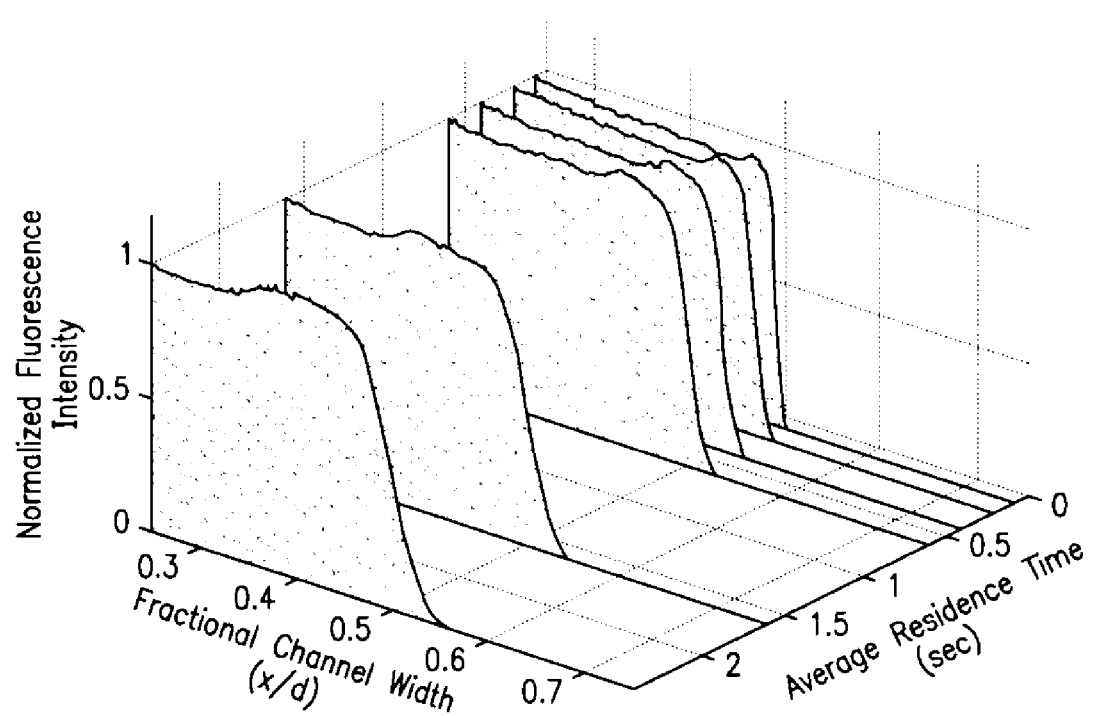
FIG. 14 illustrates the results from Experiment 3 (particle deceleration using a LJP). The contents of the microfluidic channel are described in Table 1. The normalized fluorescence intensity profiles are shown for average residence times of 0.075, 0.2, 0.4, 0.6, 1.6, and 2.7 seconds. The behavior of the system shows significant departures from the predictions for a freely-diffusing species indicating that the LJP has a measurable effect on the distribution of fluorescein in the channel.
Figure 15:
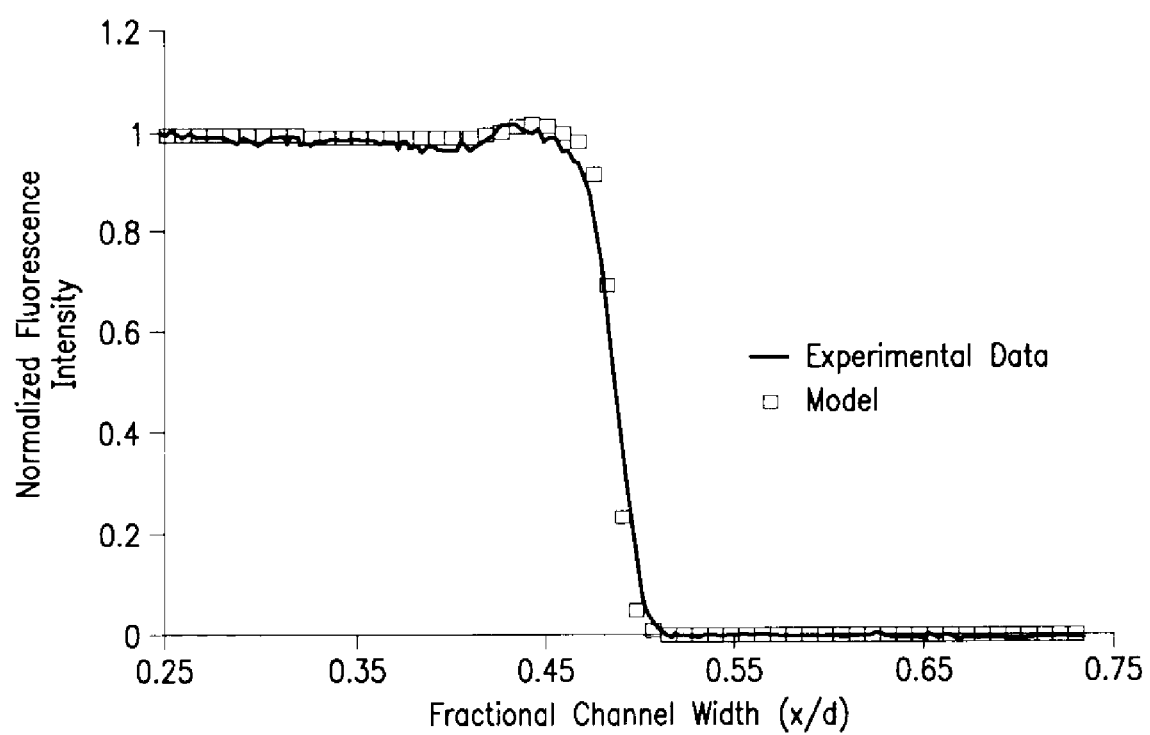
FIG. 15 illustrates a comparison of experimental data from Experiment 3 (—) to the model (□). The results from the mathematical model are compared to the experimental results at an average residence time of 0.4 sec. Qualitative agreement is seen in that the model predicts the major features of the experimental data.

In Experiment 3, the unlabeled solution contained a high concentration of $Na_2SO_4$ and the labeled solution contained none. A LJP was predicted in this case because $Na^+$ ($1.33 \times 10^{-5}$ $cm^2$/sec) diffuses 23% faster than $SO_4^{-2}$ ($1.03 \times 10^{-5}$ $cm^2$/sec) (Lide, D. R., CRC Handbook of Chemistry and Physics, 75th ed.; CRC Press, Cleveland, Ohio:, 1995). In this experiment the anionic species diffused faster than the cationic species, which was the opposite of Experiment 2. Therefore, the sign of the electric field generated in this case was anticipated to be opposite to that of the Experiment 2. In this case we expected that the fluorescein transport across the channel would be decelerated by the LJP, resulting in a concentration of the fluorescein in its solution of origin. The experimental concentration profiles are shown in FIG. 14. These concentration profiles show that there was electrophoretic transport of the tracer molecule in the opposite direction of the diffusive transport. This was evidenced by the increase in the normalized intensity in the labeled solution, which indicated that fluorescein has accumulated in this region. This accumulation of fluorescein was predicted by the mathematical model, as shown in FIG. 15.

The nature of the accumulation zone is a function of the residence time. In FIG. 13, we see that the accumulation was formed almost immediately after the fluids were brought into contact, and took on its largest magnitude at this time, as measured by the height of the accumulation. This is consistent with the prediction that during the early stages of potential formation, the field strength would be highly localized at the center of the channel and takes on its highest values. As the gradient of the potential-forming species (in this case $Na_2SO_4$) became less steep, the accumulation zone became broader with a lower magnitude. The region broadened because the field began to occupy larger fractions of the channel, thereby affecting more of the fluorescein molecules. The magnitude of the bump decreases with residence time. This was because field strength and therefore the electrophoretic velocity of the fluorescein decreased, allowing fluorescein to diffuse down the newly formed concentration gradients.

It has been demonstrated herein that the formation of the junction potential can have a measurable impact on the rate of mass transport between the streams. The results from the experiments described above show significant acceleration or deceleration of mass transport. The distribution of the mass in the channel was also measured when the labeled solution contained high salt concentrations.

An interesting result was that for sufficiently small residence times, the concentration profiles for various times intersected at a common point. This is the expected behavior for the diffusion only experiments, where the profiles intersected at the equilibrium concentration, but an unanticipated result for the other cases. In the case where an LJP was formed, the concentration at which the intersection occurs is displaced from the equilibrium concentration, but still occurred at the centerline of the channel. The concentration at the intersection was higher when the electrophoretic flux and the diffusive flux were in the same direction, and lower when the fluxes were opposed because of the relative rates of diffusive and electrophoretic fluxes.

Electrophoresis Without Applied Voltage

Figure 16:
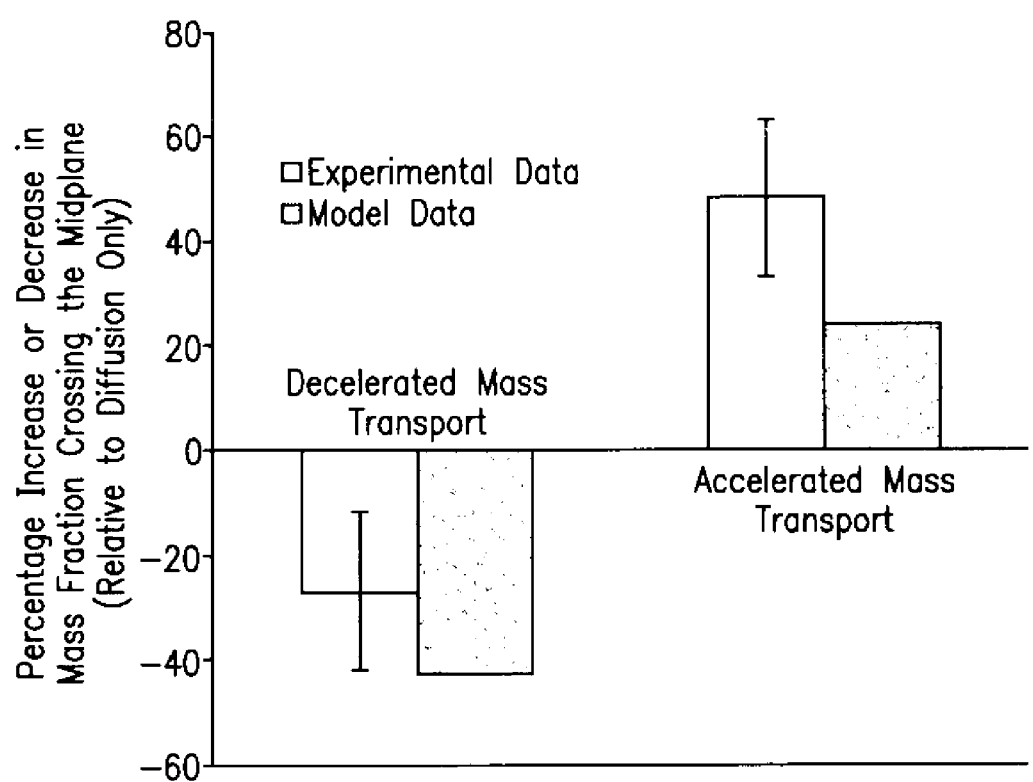
FIG. 16 is a comparison of experimental results to the model predictions. The percent increase or decrease of mass crossing the channel midline relative to the diffusion-only experiment is shown for a mean residence time of 2.4 Sec. It can be seen that the LJP induces a significant change in the net flux across the channel midplane. The model predictions under-predict the effect of the LJP. The error bars represent the standard deviation from three replicate experiments.

Comparison of these three experimental results shows that transverse electrophoresis was achieved without the application of an external voltage by using the liquid junction potential. To compare the different experiments, the percentage of the fluorescein that crossed the midline in a given time was computed (FIG. 16). The percentage of mass crossing the midline was increased by 60% relative to diffusion only when the junction potential was generated with NaCl, while the percentage of mass crossing the midline was decreased by 34% relative to diffusion only when the junction potential was generated with $Na_2SO_4$. This represents a significant change in the rate of mass transport between the streams. This result is even more striking when one considers how small the potentials generated in these experiments were (approximately 3–5 µV).

Larger potentials for the LJP are possible using gradient-forming species with a higher difference in mobility. The magnitude of the potential may also be increased by using higher concentration ratios at lower overall concentrations. By taking these approaches an electrophoretic migration can be established that is larger than the magnitude of the diffusive flux. In this case, the net flux of fluorescein is against its concentration gradient. While the junction potential persists, it is possible to prevent the diffusion of a charged species out of its original fluid stream.

The percentage of the mass crossing the midline was shown to be significantly affected by the LJP. This indicates that the LJP can induce an electrophoretic flux that acts in conjunction or opposition with the diffusive flux, thereby accelerating or decelerating the mass transport across the midline. Examining the shapes of the concentration profiles in the channel illustrates the effects of the junction potential more dramatically. The shapes of the profiles in the presence of a junction potential, which is to say the formation of a bump (accumulation) or a dip (depletion) in the concentration profile, differ dramatically from the shapes of standard diffusion profiles. If, for example, one were trying to measure the diffusion coefficient of a charged species in a T-sensor by previous methods such as that of Kamholz (Kamholz, A. E., et al., Anal Chem 1999, 71, 5340–5347) such concentration profiles would lead to significantly erroneous results. These findings demonstrate the need to account for the LJP in micro total analytical systems (µTAS) applications where significant gradients (approximately one order of magnitude based on calculations using the Henderson Equation (Henderson, P., Z. Phys. Chem. 1907, 59, 118–127; Henderson, P., Z. Phys. Chem. 1908, 63, 325–345) in ionic strength are formed. This need is especially manifest in systems that rely on tracking the spatial distribution of a species in a channel transverse to the direction of flow. The magnitude and relative importance of these potentials (generated either deliberately or as artifacts of using complex solutions) should be analyzed case by case. This invention provides a method to determine and correct such concentration measurements to take account of the contribution of LJPs when the solutions contain ionic species (gradient-forming species) capable of forming LJPs.

These experiments employed the addition of 1 M salt to one of the fluids. While this is a very high salt content, and well beyond the limit of ideal solutions where the effects of activity can be ignored, the resulting concentration ratio is not extreme. In this instance, the pH sensitivity of fluorescein mandates a significant buffer concentration in the low conductivity solution, thereby requiring a prohibitively high concentration of added salt in the high conductivity stream. However, it is well known that the magnitude of the junction potential depends only on the ratio of ionic strengths (MacInnes, D. A., *The Principles of Electrochemistry;* Reinhold Publishing, New York 1939; Lewis, G. N., Sargent, L. W., *J. Am. Chem. Soc.* 1909, 31, 363–367.; MacInnes, D. A., *J. Am. Chem. Soc.* 1915, 37, 2301–2307; Lamb, A. B., et al., *J. Am. Chem. Soc.* 1920, 42, 229–237; MacInnes, D. A., et al., *J. Am. Chem. Soc.* 1921, 43, 2563–2573; Bard and Faulkner, "Electrochemical Methods: Fundamentals and Applications", $2^{nd}$ ed., John Wiley and Sons, New York, 2001, p. 64) of the two solutions. Because the sodium salt form of the buffering compound was used, adding one molar salt to one of the streams leads to a concentration ratio of approximately 7,700. Neglecting the differences in activity, the junction potentials generated here would be identical to the junction potentials generated in a system where one stream had a salt concentration of 10 μM and the other had a concentration of 1.3 nM. Larger concentration ratios and therefore junction potentials can be achieved at lower total concentrations if the buffering demands of the system are not as stringent. Those of ordinary skill in the art are able to readily determine appropriate buffer/electrolyte choices and concentrations for a given system to establish the necessary ratios for formation of LJPs using the teachings hereof.

In addition, the magnitude of the junction potential depends on the ratio of the diffusivities of the ions in solution. Here we have chosen NaCl and $Na_2SO_4$, which have very similar diffusion coefficients, as our gradient-forming species. Potentials with significantly higher magnitudes may be achieved using gradient-forming species with larger differences in mobilities at particular pH as known to the art, for example, a charged polymer with a small counterion. Such charged polymers are known in the art and include, among others, Polyethyleneimine (PEI), Poly(L-lysine) (PL), Poly(lactic acid) (PLA), Poly(glycolic acid) (PGA), Poly(lactic-co-glycolic acid) (PLGA), Polyamidoamine (PAMAM) dendrimers, Deoxyribonucleic acid (DNA), Ribonucleic acid (RNA), Dextran-sulfate, and many other biological polymers, and most proteins.

While it is true that significantly larger potentials can be generated with an applied voltage, the formation of junction potentials is an attractive way to achieve electrophoresis transverse to the direction of flow because it requires no special fabrication techniques, can be operated in a continuous manner, and it is "self-powering." Means for increasing the magnitude of the potential and the lifetime of the field include, for example, using sodium dextran sulfate (Sigma, St. Louis, Mo., USA) as the LJP-forming electrolyte (data not shown). This is representative of the case detailed above, whereby the LJP is formed using gradient-forming species with a more substantial difference in the diffusivity of the component species ($Na^+$ and dextran sulfate).

Although the model provided herein is not a complete description of the physical phenomena occurring, it semi-quantitatively predicts the effects of the liquid junction potential, and is a legitimate and effective tool to approximate the properties of junction potentials produced by various solution conditions. This allows the model to be used to predict the magnitude and duration of the LJP within an order of magnitude.

All references cited herein are incorporated in their entirety to the extent not inconsistent herewith.

Those skilled in the art will appreciate that the invention described herein is susceptible to variations and modifications other than those specifically described. It is to be understood that the invention includes all such variations and modifications which fall within its spirit and scope.

We claim:

1. A method for controlling the transport of a charged particle in a first fluid stream with respect to an interface formed by direct contact between said first fluid stream and a second fluid stream in adjacent laminar flow therewith in a microfluidic channel, the method comprising creating a liquid junction potential at said interface by providing ions in at least one of said fluids of charge, concentration, mobility, and/or charge magnitude selected to accelerate or decelerate movement of said charged particle with respect to said interface.

2. The method of claim 1, wherein said interface is non-linear.

3. The method of claim 1 wherein charged particles are focused in one dimension within a microfluidic channel, the method comprising the steps of:
   a) introducing a core fluid containing a charged particle into said microfluidic channel; and
   b) introducing a sheath fluid into said microfluidic channel such that the sheath fluid surrounds the core fluid on at least two opposite sides of the core fluid and such that the core fluid and the sheath fluid form a fluid interface and flow in adjacent laminar flow in said microfluidic channel;
   said sheath fluid comprising a first set of gradient-forming species, said first set of gradient-forming species comprising at least a first ion and a second ion, wherein said first ion has a charge opposite the charge of said particle and said first ion has a higher mobility than said second ion and wherein said second ion has the same charge as said particle and wherein when said first set of gradient-forming species is present in said core fluid, said first ion is present in higher concentration in said sheath fluid than in the core fluid;
   whereby a liquid junction potential is formed at the interface between said sheath fluid and said core fluid and charged particles are focused in said core fluid.

4. The method of claim 3 wherein said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

5. The method of claim 1 wherein charged particles are extracted from a fluid within a microfluidic channel, the method comprising the steps of:
   a) introducing a core fluid containing a first charged particle into said microfluidic channel; and
   b) introducing a sheath fluid into said microfluidic channel such that the sheath fluid surrounds the core fluid on at least two opposite sides of the core fluid and a fluid interface is formed between the core fluid and the sheath fluid and said core and sheath fluids flow in adjacent laminar flow in said microfluidic channel;
   wherein said sheath fluid comprises a first set of gradient-forming species, said first set of gradient-forming species comprising at least a first ion and a second ion, wherein said first ion has the same charge of said particle and said first ion has a higher mobility than said second ion and wherein said second ion has the opposite charge of said particle and wherein when said first set of gradient-forming species is present in said core fluid said first ion is present in higher concentration in the sheath fluid than in the core fluid;

whereby a liquid junction potential is formed at the interface between said sheath fluid and said core fluid and said charged particles are extracted from said core fluid.

6. The method of claim 5 wherein said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

7. The method of claim 1 wherein charged particles are separated within a microfluidic channel, the method comprising the steps of:
   a) introducing a core fluid containing at least a first and a second charged particle into said microfluidic channel, wherein each of said charged particles has the same charge and each of said charged particles has a different mobility; and
   b) introducing a sheath fluid into said microfluidic channel such that the sheath fluid surrounds the core fluid on at least two opposite sides of the core fluid and a fluid interface is formed between the core fluid and the sheath fluid and said core fluid and said sheath fluids flow in adjacent laminar flow in said microfluidic channel;
   wherein said sheath fluid comprises a first set of gradient-forming species, said first set of gradient-forming species comprising at least a first ion and a second ion, wherein said first ion has the same charge of said charged particles and said first ion has a higher mobility than said second ion and wherein said second ion has the opposite charge of said particle and wherein when said first set of gradient-forming species is present in said core fluid said first ion is present in higher concentration in the sheath fluid than in the core fluid;
   whereby a liquid junction potential is formed at the interface between said sheath fluid and said core fluid and said charged particles are separated.

8. The method of claim 7 wherein said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

9. The method of claim 1 wherein charged particles of opposite charge are extracted and separated from a fluid within a microfluidic channel, the method comprising the steps of:
   a) introducing a core fluid containing at least first and second charged particles of opposite charge into said microfluidic channel, said core fluid comprising a set of core gradient-forming species comprising at least first and second ions; and
   b) introducing a first sheath fluid into said microfluidic channel to form a fluid interface with said core fluid, said first sheath fluid comprising a first set of sheath gradient-forming species comprising first and second ions that are the same as the first and second ions in the set of core gradient-forming species and wherein the ionic concentration of the first sheath fluid is higher than the ionic concentration of said core fluid and said first sheath fluid is in adjacent laminar flow with said core fluid in said microfluidic channel;
   c) introducing a second sheath fluid into said microfluidic channel to form a fluid interface with said core fluid, said second sheath fluid comprising a second set of sheath gradient-forming species comprising first and second ions that are the same as the first and second ions in the set of core gradient-forming species and wherein said second sheath fluid has a lower ionic concentration than the ionic concentration of said core fluid and said second sheath fluid is in adjacent laminar flow with said core fluid in said microfluidic channel;
   wherein said first ion has the same charge of said first charged particle and has a higher mobility than said second ion and wherein said second ion has the same charge of said second particle;
   whereby a liquid junction potential is formed at each fluid interface between said sheath fluids and said core fluid and said oppositely charged particles are separated and extracted from said core fluid.

10. The method of claim 9 wherein the ionic concentrations of all of the sets of gradient-forming species are equal and
   said set of core gradient-forming species is different than said first set of sheath gradient-forming species;
   said second set of sheath gradient-forming species is different from said core gradient-forming species and said first set of sheath gradient-forming species;
   said first ion in said first set of sheath gradient-forming species has higher mobility than said first ion in said core gradient-forming species;
   said first ion in said core gradient-forming species has higher mobility than said first ion in said second set of sheath gradient-forming species; and
   the second ion in each set of gradient-forming species is the same.

11. The method of claim 1 wherein charged particles are focused in two dimensions within a microfluidic channel, the method comprising the steps of:
   a) introducing a core fluid containing a charged particle into said microfluidic channel; and
   b) introducing a sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel;
   wherein said sheath fluid comprises a first set of gradient-forming species, said first set of gradient-forming species comprising at least a first ion and a second ion, wherein said first ion has a charge opposite the charge said charged particle and said first ion has a higher mobility than said second ion and wherein said second ion has the same charge as said particle and wherein when said first set of gradient forming species are present in said core fluid, said first ion is present in higher concentration in the sheath fluid than in the core fluid;
   whereby a liquid junction potential is formed at the interface between said sheath fluid and said core fluid and said charged particles are focused within said core fluid.

12. The method of claim 11 wherein said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

13. The method of claim 1 wherein charged particles are extracted from a fluid stream within a microfluidic channel, the method comprising the steps of:
   a) introducing a core fluid containing a charged particle into said microfluidic channel; and
   b) introducing a sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel
   wherein said sheath fluid comprises a first set of gradient-forming species, said first set of gradient-forming species comprising at least a first ion and a second ion, wherein said first ion has the same charge as said charged particle and said first ion has a higher mobility than said second ion and wherein said second ion has the opposite charge of said charged particle and wherein when said first set of gradient forming species are present in said core fluid, said first ion is present in higher concentration in the sheath fluid than in the core fluid;
   whereby a liquid junction potential is formed at the interface between said sheath fluid and said core fluid and said charged particles are extracted from said core fluid.

14. The method of claim 13 wherein said core fluid comprises a second set of gradient-forming species wherein the ionic concentrations of the first and second sets of gradient-forming species are equal, the second ion in each set of gradient-forming species is the same, and the first ion in the second set of gradient-forming species has a lower mobility than the first ion in the first set of gradient-forming species.

15. The method of claim 1 wherein charged particles are focused in two dimensions within a microfluidic channel, the method comprising the steps of:
   a) introducing a core fluid containing a charged particle into said microfluidic channel; and
   b) introducing a sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel
   wherein said core fluid comprises a first set of gradient-forming species, said first set of gradient-forming species comprising at least a first ion and a second ion, wherein said first ion has the opposite charge of said charged particle and said first ion has a lower mobility than said second ion and wherein said second ion has the same charge as said charged particle and wherein when said first set of gradient forming species is present in said sheath fluid, said ions are present in higher concentration in the core fluid than in the sheath fluid;
   whereby a liquid junction potential is formed at the interface between said sheath fluid and said core fluid and said charged particles are focused in said core fluid.

16. The method of claim 15 wherein said sheath fluid comprises a second set of gradient-forming species wherein the ionic concentrations of the first and second sets of gradient-forming species are equal, the second ion in each set of gradient-forming species is the same, and the first ion in the second set of gradient-forming species has a higher mobility than the first ion in the first set of gradient-forming species.

17. The method of claim 1 wherein charged particles are extracted from a fluid stream within a microfluidic channel, the method comprising the steps of:
   a) introducing a core fluid containing a charged particle into said microfluidic channel; and
   b) introducing a sheath fluid into said microfluidic channel such that the sheath fluid surrounds the core fluid on all sides of the core fluid to form a fluid interface between said core fluid and said sheath fluid and such that the core fluid and the sheath fluid flow in adjacent laminar flow in said microfluidic channel
   wherein said core fluid comprises a first set of gradient-forming species, said first set of gradient-forming species comprising at least a first ion and a second ion, wherein said first ion has the same charge as said charged particle and said first ion has a lower mobility than said second ion and wherein said second ion has the opposite charge of said charged particle and wherein when said first set of gradient forming species is present in said sheath fluid said first ion is present in higher concentration in said core fluid than in said sheath fluid;
   whereby a liquid junction potential is formed at the interface between said sheath fluid and said core fluid and said charged particles are extracted from said core fluid.

18. The method of claim 17 wherein said sheath fluid comprises a second set of gradient-forming species wherein the ionic concentrations of the first and second sets of gradient-forming species are equal, the first ion in each set of gradient-forming species is the same, and the second ion in the first set of gradient-forming species has a higher mobility than the second ion in the first set of gradient-forming species.

19. The method of claim 1 wherein the mixing of charged particles is accelerated between two or more fluids within a microfluidic channel, the method comprising the steps of:
   a) introducing a first fluid containing a negatively charged particle into said microfluidic channel; and
   b) introducing at least a second fluid into said microfluidic channel such that a fluid interface is formed between the first fluid and the second fluid and the first fluid and the second fluid flow in adjacent laminar flow in said microfluidic channel
   wherein said first fluid comprises a first set of gradient-forming species, said first set of gradient-forming species comprising a cation and an anion, wherein said cation has a higher mobility than said anion and wherein when said first set of gradient forming species is present in said second fluid, said ions of the first set of gradient forming species are present in lower concentration in said second fluid than in said first fluid;
   whereby a liquid junction potential is formed at the interface between said first fluid and said second fluid and the mixing of said negatively-charged particles into said second fluid is accelerated.

20. The method of claim 19 wherein said second fluid comprises a second set of gradient-forming species wherein the ionic concentrations of the first and second sets of gradient-forming species are equal, the anion in each set of gradient-forming species is the same, and the cation in the first set of gradient-forming species has a higher mobility than the cation in the second set of gradient-forming species.

21. The method of claim 19 wherein said second fluid comprises a second set of gradient-forming species wherein the ionic concentrations of the first and second sets of gradient-forming species are equal, the cation in each set of gradient-forming species is the same, and the anion in the second set of gradient-forming species has a higher mobility than the anion in the first set of gradient-forming species.

22. The method of claim 1 wherein the mixing of charged particles is decelerated between two or more fluids within a microfluidic channel, the method comprising the steps of:
   a) introducing a first fluid containing a positively charged particle into said microfluidic channel; and
   b) introducing at least a second fluid into said microfluidic channel such that a fluid interface is formed between the first fluid and the second fluid and the first fluid and the second fluid flow in adjacent laminar flow in said microfluidic channel
   wherein said first fluid comprises a first set of gradient-forming species, said first set of gradient-forming species comprising a cation and an anion, wherein said cation has a higher mobility than said anion and wherein when said first set of gradient forming species is present in said second fluid said ions are present in higher concentration in said first fluid than in said second fluid;
   whereby a liquid junction potential is formed at the interface between said sheath fluid and said core fluid and said mixing of said positively-charged particles into said second fluid is decelerated.

23. The method of claim 22 wherein said second fluid comprises a second set of gradient-forming species wherein the ionic concentrations of the first and second sets of gradient-forming species are equal, the anion in each set of gradient-forming species is the same, and the cation in the first set of gradient-forming species has a higher mobility than the cation in the second set of gradient-forming species.

24. The method of claim 22 wherein said second fluid comprises a second set of gradient-forming species wherein the ionic concentrations of the first and second sets of gradient-forming species are equal, the cation in each set of gradient-forming species is the same, and the anion in the second set of gradient-forming species has a higher mobility than the anion in the first set of gradient-forming species.

25. The method of claim 1 wherein the mixing of charged particles is accelerated between two or more fluids within a microfluidic channel, the method comprising the steps of:
   a) introducing a first fluid containing a positively charged particle into said microfluidic channel; and
   b) introducing at least a second fluid into said microfluidic channel such that a fluid interface is formed between the first fluid and the second fluid and the first fluid and the second fluid flow in adjacent laminar flow in said microfluidic channel
   wherein said second fluid comprises a first set of gradient-forming species, said first set of gradient-forming species comprising a cation and an anion, wherein said cation has a higher mobility than said anion and wherein when said first set of gradient forming species is present in said first fluid said ions are present in higher concentration in said second fluid than in said first fluid;
   whereby a liquid junction potential is formed at the interface between said first and second fluids and the mixing of said positively-charged particle into said second fluid is accelerated.

26. The method of claim 25 wherein said first fluid comprises a second set of gradient-forming species wherein the ionic concentrations of the first and second sets of gradient-forming species are equal, the cation in each fluid is the same, and the anion in the first fluid has a higher mobility than the anion in the second fluid.

27. The method of claim 25 wherein said first fluid comprises a second set of gradient-forming species wherein the ionic concentrations of the first and second sets of gradient-forming species are equal, the anion in each set of gradient-forming species is the same, and the cation in the second set of gradient-forming species has a higher mobility than the cation in the first set of gradient-forming species.

28. The method of claim 1 wherein the mixing of charged particles is decelerated between two or more fluids within a microfluidic channel, the method comprising the steps of:
   a) introducing a first fluid containing a negatively charged particle into said microfluidic channel; and
   b) introducing at least a second fluid into said microfluidic channel such that a fluid interface is formed between the first fluid and the second fluid and the first fluid and the second fluid flow in adjacent laminar flow in said microfluidic channel
   wherein said second fluid comprises a first set of gradient-forming species, said first set of gradient-forming species comprising a cation and an anion, wherein said cation has a higher mobility than said anion and wherein when said first set of gradient forming species is present in said first fluid said ions are present in higher concentration in said second fluid than in said first fluid;
   whereby a liquid junction potential is formed at the interface between said first fluid and said second fluid and said mixing of said negatively-charged particles into said second fluid is decelerated.

29. The method of claim 28 wherein said first fluid comprises a second set of gradient-forming species wherein the ionic concentrations of the first and second sets of gradient-forming species are equal, the cation in each fluid is the same, and the anion in the first fluid has a higher mobility than the anion in the second fluid.

30. The method of claim 28 wherein said first fluid comprises a second set of gradient-forming species wherein the ionic concentrations of the first and second sets of gradient-forming species are equal, the anion in fluid is the same, and the cation in the second fluid has a higher mobility than the cation in the first fluid.

31. The method of claim 1 wherein the rate of a reaction in a microfluidic channel is enhanced, the method comprising the steps of:
   a) introducing a first fluid containing a first reactive charged particle into said microfluidic channel;
   b) introducing a second fluid containing a second reactive charged particle into said microfluidic channel such that a fluid interface is formed between said first and second fluids and said first and second fluids are in adjacent laminar flow within said microfluidic channel;
   wherein:
   said first reactive particle has the opposite charge of said second reactive particle;
   said second fluid comprises a first set of gradient-forming species;
   said first set of gradient-forming species comprising a first ion and a second ion wherein said first ion has a charge opposite the charge of said second reactive charged particle and of said second ion and said first ion has a higher mobility than said second ion;

and when said first set of gradient forming species is present in said first fluid said ions of the first set of gradient forming species are present in higher concentration in said second fluid than in said first fluid;

whereby a liquid junction potential is formed at said interface between said first and second fluids and the reaction of said oppositely-charged particles is enhanced.

32. The method of claim 31 wherein said first fluid comprises a second set of gradient-forming species wherein the ionic concentrations of the first and second sets of gradient-forming species are equal, the second ion in each fluid is the same, and the first ion in the second fluid has a higher mobility than the first ion in the first fluid.

33. A method of making a microfluidic device for establishing a liquid junction potential, said method comprising:

a) providing a microfluidic channel in said device;
b) flowing into said microfluidic channel at least a first and a second fluid stream in parallel laminar flow in said microfluidic channel to form at least one fluid interface formed by direct contact between the first and second streams;
c) providing charged particles contained in at least one of said fluid streams;
d) providing ions contained in at least one of said fluid streams of a charge, concentration, mobility and/or charge magnitude selected to control movement of said charged particles with respect to said interface.

34. The method of claim 33 wherein said interface is non-linear.

* * * * *